(12) United States Patent
Yan et al.

(10) Patent No.: US 8,623,995 B2
(45) Date of Patent: Jan. 7, 2014

(54) PEPTIDE CONJUGATES AND FLUORESCENCE DETECTION METHODS FOR INTRACELLULAR CASPASE ASSAY

(75) Inventors: Xiongwei Yan, Dublin, CA (US); Sheri Miraglia, Belmont, CA (US); Pau Miau Yuan, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/814,642

(22) Filed: Jun. 14, 2010

(65) Prior Publication Data

US 2011/0097758 A1 Apr. 28, 2011

Related U.S. Application Data

(60) Continuation of application No. 12/642,552, filed on Dec. 18, 2009, now abandoned, which is a continuation of application No. 12/479,714, filed on Jun. 5, 2009, now abandoned, which is a continuation of application No. 11/427,756, filed on Jun. 29, 2006, now abandoned, which is a division of application No. 11/320,162, filed on Dec. 27, 2005, now abandoned, which is a division of application No. 09/862,224, filed on May 21, 2001, now Pat. No. 6,979,530.

(51) Int. Cl.
*C07K 1/04* (2006.01)
*C07K 1/13* (2006.01)
*C07K 1/113* (2006.01)

(52) U.S. Cl.
USPC .......................................... 530/334; 530/345

(58) Field of Classification Search
None
See application file for complete search history.

(56) References Cited

U.S. PATENT DOCUMENTS

| | | | | |
|---|---|---|---|---|
| 5,352,756 | A | * | 10/1994 | Meldal .............................. 525/50 |
| 5,545,698 | A | * | 8/1996 | Barany et al. .................. 525/420 |
| 5,547,849 | A | | 8/1996 | Baer et al. |
| 5,605,809 | A | * | 2/1997 | Komoriya et al. ............... 435/23 |
| 5,698,411 | A | | 12/1997 | Lucas et al. |
| 5,714,342 | A | | 2/1998 | Komoriya et al. |
| 5,936,087 | A | | 8/1999 | Benson et al. |
| 5,976,822 | A | | 11/1999 | Landrum et al. |
| 5,989,835 | A | | 11/1999 | Dunlay et al. |
| 6,051,719 | A | | 4/2000 | Benson et al. |
| 6,103,479 | A | | 8/2000 | Taylor |
| 6,127,139 | A | | 10/2000 | Te Koppele et al. |
| 6,130,745 | A | | 10/2000 | Manian |
| 6,166,202 | A | | 12/2000 | Simmonds et al. |
| 6,181,413 | B1 | | 1/2001 | Manian |
| 6,235,493 | B1 | | 5/2001 | Bissell et al. |
| 6,248,904 | B1 | | 6/2001 | Zhang et al. |
| 6,465,644 | B1 | * | 10/2002 | Yan et al. ........................ 544/99 |
| 6,583,168 | B1 | | 6/2003 | Menchen et al. |
| 2010/0273943 | A1 | | 10/2010 | Yan et al. |

FOREIGN PATENT DOCUMENTS

| | | | |
|---|---|---|---|
| EP | 1033411 | | 9/2000 |
| WO | 97/29154 | | 8/1997 |
| WO | 99/18856 | | 4/1999 |
| WO | WO99/27020 | * | 6/1999 |
| WO | 00/50635 | | 8/2000 |
| WO | 00/64988 | | 11/2000 |
| WO | WO00/66615 | * | 11/2000 |
| WO | 00/73437 | | 12/2000 |
| WO | 00/75160 | | 12/2000 |
| WO | 02/44416 | | 6/2002 |
| WO | 03/057723 | | 7/2003 |

OTHER PUBLICATIONS

International Search Report from PCT/US02/15713 mailed Dec. 18, 2003.
Miraglia, et al., "Homogeneous Cell- and Bead-Based Assays for High Throughput Screening Using Fluorometric Microvolume Assay Technology", *Journal of Biomolecular Screening vol. 4*, No. 4,, 1999, 193-204.
Swartzman, et al., "A Homogeneous and Multiplexed Immunoassay for High-Throughput Screening Using Fluorometric Microvolume Assay Technology", *Analytical Biochemistry*, 271, 1999, 143-151.
Thornberry, "A Combinatorial Approach Defines Specificities of Members of the Caspase Family and Granzyme B", *J Biol Chem*, 272, 1997, 17907-17911.
Thornberry, et al., "Caspases: Enemies Within", *Science*, vol. 281, Aug. 28, 1998, 1312-1316.
Xu, Xiang et al., "Detection of programmed cell death using fluorescence energy transfer", *Nucleic Acids Res.*, 26, 1998, 2034-2035.

* cited by examiner

*Primary Examiner* — Karen Canella
(74) *Attorney, Agent, or Firm* — Applied Biosystems, LLC

(57) ABSTRACT

Polypeptides labelled with a donor and acceptor pair of dyes selected from a dibenzorhodamine dye and a diamino-benzophenoxazine dye are peptide conjugates which are useful for intracellular and bead-based assays with fluorescence detection. Peptide conjugates with a caspase-recognition site undergo cleavage into peptide fragments which may be detected, located, and quantitated by the changes in fluorescence. Intracellular cleavage of peptide conjugates is correlated with apoptosis.

2 Claims, 14 Drawing Sheets

SEQUENCE LISTING

<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

Asp Glu Val Asp
1

<210> SEQ ID NO 2
<211> LENGTH: 8
<212> TYPE: PRT
<213> ORGANISM: Homo sapiens

<400> SEQUENCE: 2

Gly Asp Glu Val Asp Gly Ile Lys

```
<210> SEQ ID NO 3
<211> LENGTH: 8
<212> TYPE: PRT
<213> ORGANISM: Homo sapiens

<400> SEQUENCE: 3

Gly Leu Glu Thr Asp Gly Ile Lys
1               5
```

PEPTIDE CONJUGATES AND FLUORESCENCE DETECTION METHODS FOR INTRACELLULAR CASPASE ASSAY

I. CROSS REFERENCE TO RELATED APPLICATIONS

This application is a continuation of application Ser. No. 12/642,552, filed Dec. 18, 2009, which is a continuation of application Ser. No. 12/479,714, filed Jun. 5, 2009 (now abandoned), which is a continuation of application Ser. No. 11/427,756, filed Jun. 29, 2006 (now abandoned), which is a divisional of application Ser. No. 11/320,162, filed Dec. 27, 2005 (now abandoned), which is a divisional of application Ser. No. 09/862,224, filed May 21, 2001 (now U.S. Pat. No. 6,979,530), the disclosures of which are hereby incorporated herein by reference in their entirety.

II. FIELD OF THE INVENTION

This invention relates generally to cell biology and intracellular assays with fluorescence detection. More specifically, this invention relates to labelled peptides cleaved by caspase enzymes.

III. BACKGROUND OF THE INVENTION

The caspase family of about 12 cysteine proteases is central to the complex intracellular process of apoptosis, or programmed cell death (Thornberry, Science (1998) 281:1312-16). Caspase activation accompanies the onset of apoptosis which has been implicated in many of the major illnesses without cures. Apoptosis is characterized by a set of morphological and biochemical changes that dying cells undergo, including condensation, shrinkage, margination of chromatin, cytoplasmic vacuolization, increased density, and fragmented nucleic with dispersal of nuclear DNA. Caspase-3 has been shown to control both cytoplasmic and nuclear events associated with Fas-mediated apoptosis in vivo (Zheng, (1998) Proc. Natl. Acad. Sci. USA 95:618-23). DNase is activated by caspase in apoptotic cells (Enari, Nature (1998) 391:43-50). Caspase enzymes are good targets for small molecule inhibitors. Caspase inhibitors are potential therapeutics for certain diseases such as Alzheimers, multiple sclerosis and other neurodegenerative disorders. However, inhibiting caspases may have accompanying effect of inducing cancers and other cell proliferation effects. It is hoped that understanding the mechanisms of inducing apoptosis and inhibiting caspase activation and activity will yield drugs, e.g. to reduce damage from stroke or myocardial infarction, or prevent and treat cancer.

Peptides which include the amino acid sequence cleaved by caspases are useful probes for assaying caspase activity and thus the onset and progress of apoptosis. (Xanthoudakis, WO 00/73437; Komoriyama WO 96/13607). One critical feature of probe design is to facilitate mammalian cell membrane permeability. For high throughput drug screening it is desirable to mimic the natural state of the living cell. Therefore, the probe should enter the living cell without hypotonic shock, microinjection or other invasive or damaging techniques. For cell based high-throughput screening (HTS), another desirable property is cellular retention of the reporter dye.

Fluorescence based detection methods are important to elucidate intracellular events such as apoptosis. Enzyme substrates labelled with fluorescent dyes have been used to measure protease cleavage activity (Coyler, WO 00/50635; Weber, WO 99118856). Fluorescent enzymatic assays have been conducted on cell-based screening systems (Dunlay, U.S. Pat. No. 5,989,835; Schroeder, U.S. Pat. No. 5,355,215) in microtiter plate, high throughput formats (Marian, U.S. Pat. No. 6,130,745; Harootunian, U.S. Pat. No. 5,589,351; Heffelfinger, U.S. Pat. No. 5,784,152; Taylor, U.S. Pat. No. 6,103,479) and digitized imaging data (Baer, U.S. Pat. No. 5,547,849

Dyes which are excited and emit fluorescence at longer wavelengths are important as labels for many molecular biology experiments (Mao, U.S. Pat. No. 6,130,101; Glazer, U.S. Pat. No. 5,565,554; Waggoner, U.S. Pat. No. 5,268,486).

IV. SUMMARY

The present invention provides compositions and methods for intracellular assay, detection, and quantitation of apoptotic events. In particular, a new type of fluorogenic probe for assaying caspase enzyme activity is provided. The fluorogenic probes include red dyes which are efficiently excited with a low-cost and rugged He—Ne laser (ex 632 nm). One potential application of the invention is cell based high throughput screening (HTS) on a confocal laser scanning system.

In a first aspect, the invention includes peptide conjugate compositions comprising polypeptides covalently attached to a donor dye and an acceptor dye. The donor dye is attached to the polypeptide through a first linkage. The acceptor dye is attached to the polypeptide through a second linkage. The donor dye and acceptor dye are selected from dibenzorhodamine and diamino-benzophenoxazine structures. The donor dye is capable of absorbing light at a first wavelength and emitting excitation energy in response thereto; and the acceptor dye is capable of absorbing the excitation energy emitted by the donor dye and fluorescing at a second wavelength in response. At minimum, the fluorescence from the donor dye is quenched by the acceptor dye.

Polypeptide sequences of peptide conjugates may have a caspase-cleavage site. The polypeptide may comprise amino acid sequences of:

```
Asp-Glu-Val-Asp               SEQ ID. NO. 1

Gly-Asp-Glu-Val-Asp-Gly-Ile-Lys  SEQ ID. NO. 2
``` or homologs thereof. The side-chains of certain amino acids of the polypeptide may be protected. The donor dye or acceptor dye may be attached to the amino terminus, the carboxyl terminus, or a side-chain of an amino acid of the polypeptide. The linkage may be any bond, such as an amide or phosphate, or comprise a chain, such as an alkyldiyl, phenyldiyl, or benzydiyl, and substituted forms thereof.

The peptide conjugate may be covalently attached to a solid support. The solid support may be any material useful as a synthesis support or to which a polypeptide may be covalently attached. The solid support may be a bead, a particle, or a monolithic material with a surface or pores to which a polypeptide may be covalently attached.

In one aspect, the invention includes an assay method where the peptide conjugate is delivered or passes into eukaryotic cells. When the cells are illuminated with a light source, then fluorescence emissions can be collected, detected, analyzed, or measured. Fluorescence emissions or intensity can be measured before and after the peptide conjugate enters the cells. The peptide conjugate may be cleaved inside the cell, e.g. by a protease enzyme. The particular protease enzyme may be termed a caspase enzyme and specific for cleaving certain polypeptide sequences. The peptide conjugate may be cleaved inside the cell into two or more peptide fragments. One peptide fragment may be attached to the donor dye and another peptide fragment may be attached to the acceptor dye. The fluorescence emissions from the donor dye and the acceptor dye may be spectrally resolved and used to locate the presence of either or both dye inside the cell, as well as count cells. The cells in the assay may be treated with a substance or reagent which induces apoptosis. The cells in the assay may also be treated with a caspase inhibitor.

In another embodiment, the assay method may be conducted where cells are contained in a plurality of vessels. In any vessel, the cells may be of one type or different types of cells. The cells may be the same type grown under different conditions, e.g. in the presence of different media. Some of the cells may be treated with an apoptosis inducer or a caspase inhibitor. The plurality of vessels, an array, may be illuminated by a light source, e.g. a scanning light source. The cells may be of the same or different organisms.

In another aspect, the invention includes a solid phase method for detecting caspase activity. A peptide conjugate covalently attached by a linkage to a solid support is suspended in an aqueous solution containing a caspase in a vessel. The vessel is illuminated with a light source. Fluorescence in the vessel is detected to establish a caspase cleavage site in the polypeptide sequence in the peptide conjugate. The peptide conjugate may be cleaved into a peptide fragment that remains attached to the solid support and one or more soluble peptide fragments that are dissolved in the solution. Fluorescence from donor and acceptor dyes linked to the peptide fragments may be detected.

In another aspect, the invention includes a method of synthesizing a peptide conjugate by synthesizing a polypeptide on a solid support and reacting it with a first dye labelling reagent. The labelled polypeptide on the solid support is cleaved and reacted with a second dye labelling reagent to form the peptide conjugate with first and second dye labels. The first dye labelling reagent and the second dye labelling reagent are selected from dibenzorhodamine and diaminobenzophenoxazine structures. Each labelling reagent has a linking moiety.

In another aspect, the invention includes kits comprised of a peptide conjugate and a reagent selected from an apoptosis inducer and a caspase inhibitor. The kit may also include eukaryotic cells.

V. BRIEF DESCRIPTION OF THE FIGURES

Figure 5A:
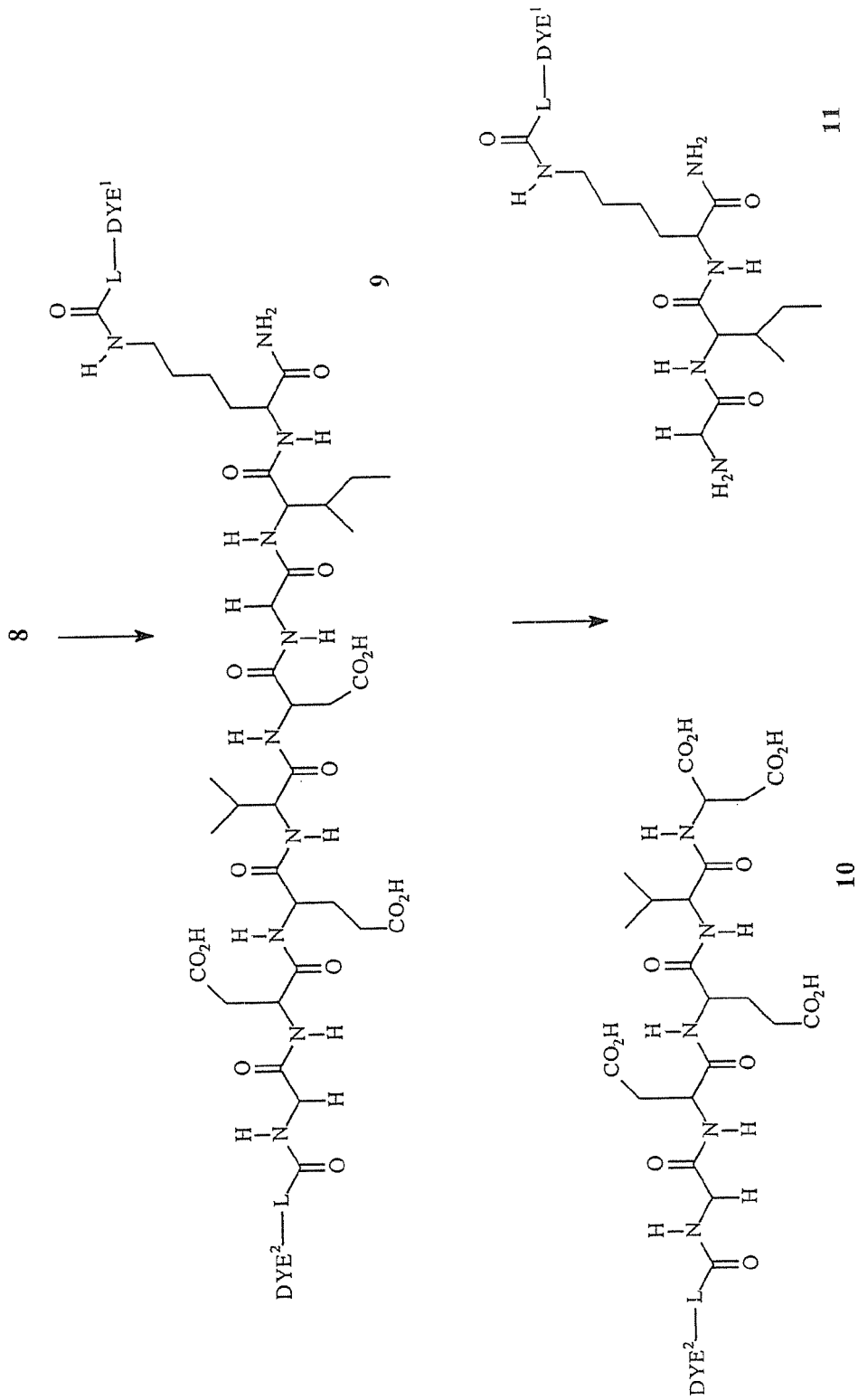

FIG. 5a shows coupling of the N-terminus amino of 8 to dye-NHS 4 to give peptide conjugate 9, and cleavage of 9 by caspase to give cleavage fragments 10 and 11.

Figure 5B:
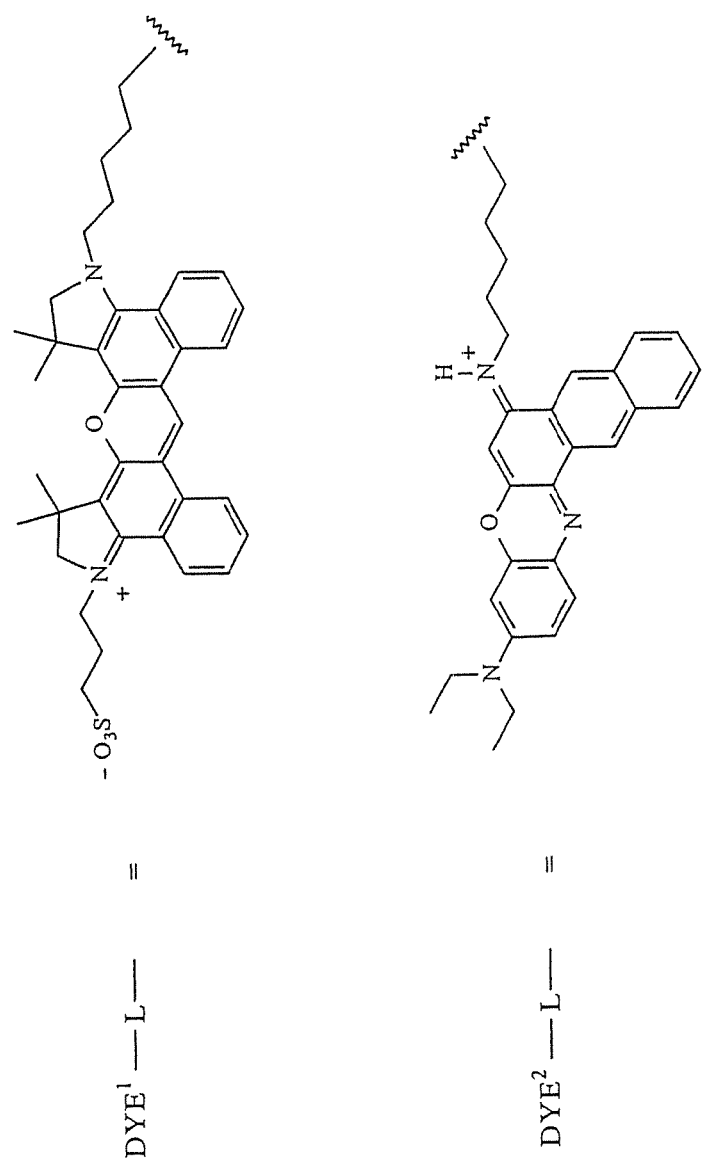

FIG. 5b shows the structures of $DYE^1$ and $DYE^2$ of 9.

Figure 6:
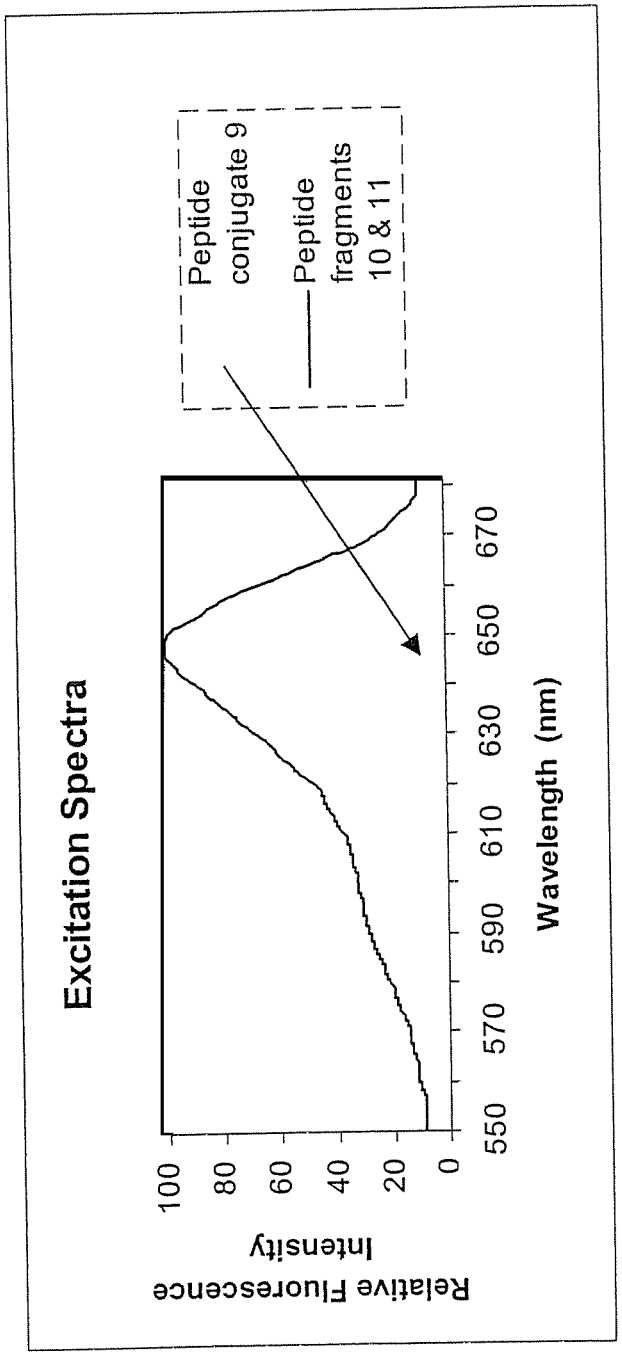

FIG. 6 shows the fluorescence excitation spectrum between 550-680 nm of peptide conjugate 9 before and after treatment with purified caspase-3. The emission wavelength was set at 700 nm.

Figure 7:
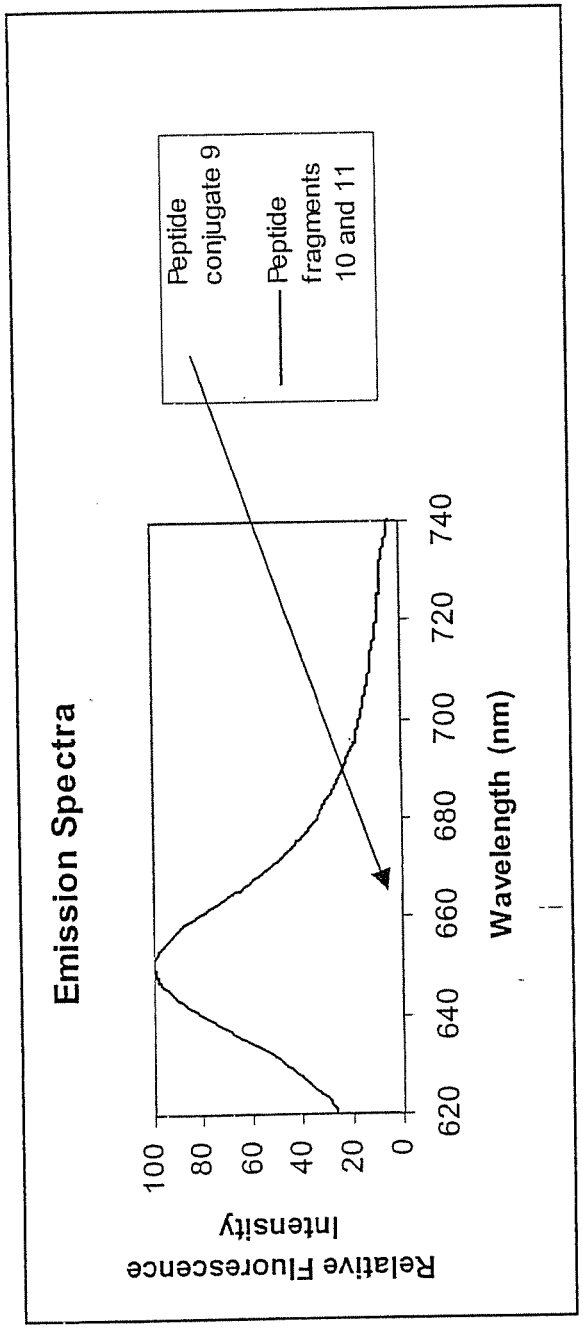

FIG. 7 shows the fluorescence emission spectrum between 620-740 nm of peptide conjugate 9 before and after treatment with purified caspase-3. The excitation wavelength was set at 600 nm.

Figure 8:
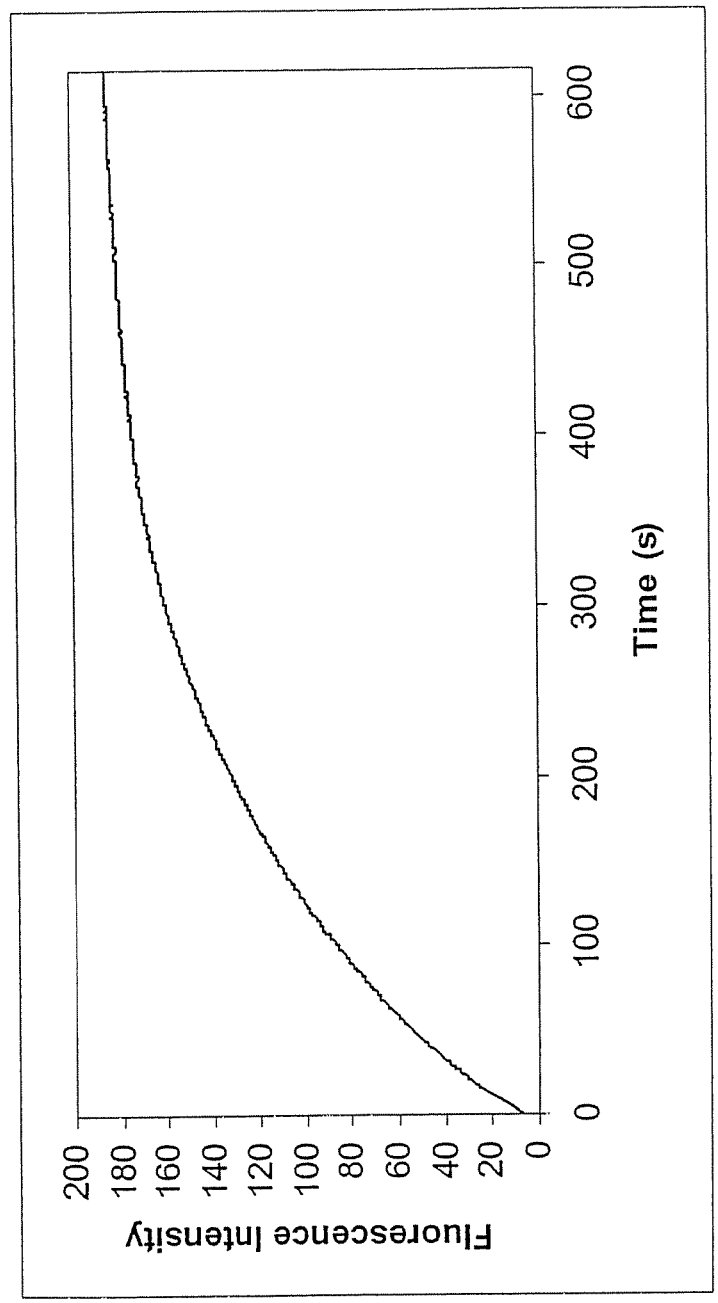

FIG. 8 shows the time-dependent increase of fluorescence emission at 650 nm by excitation at 630 nm of peptide conjugate 9 (1 µM) by in vitro cleavage after adding 0.2 ng/µl caspase-3.

Figure 9:
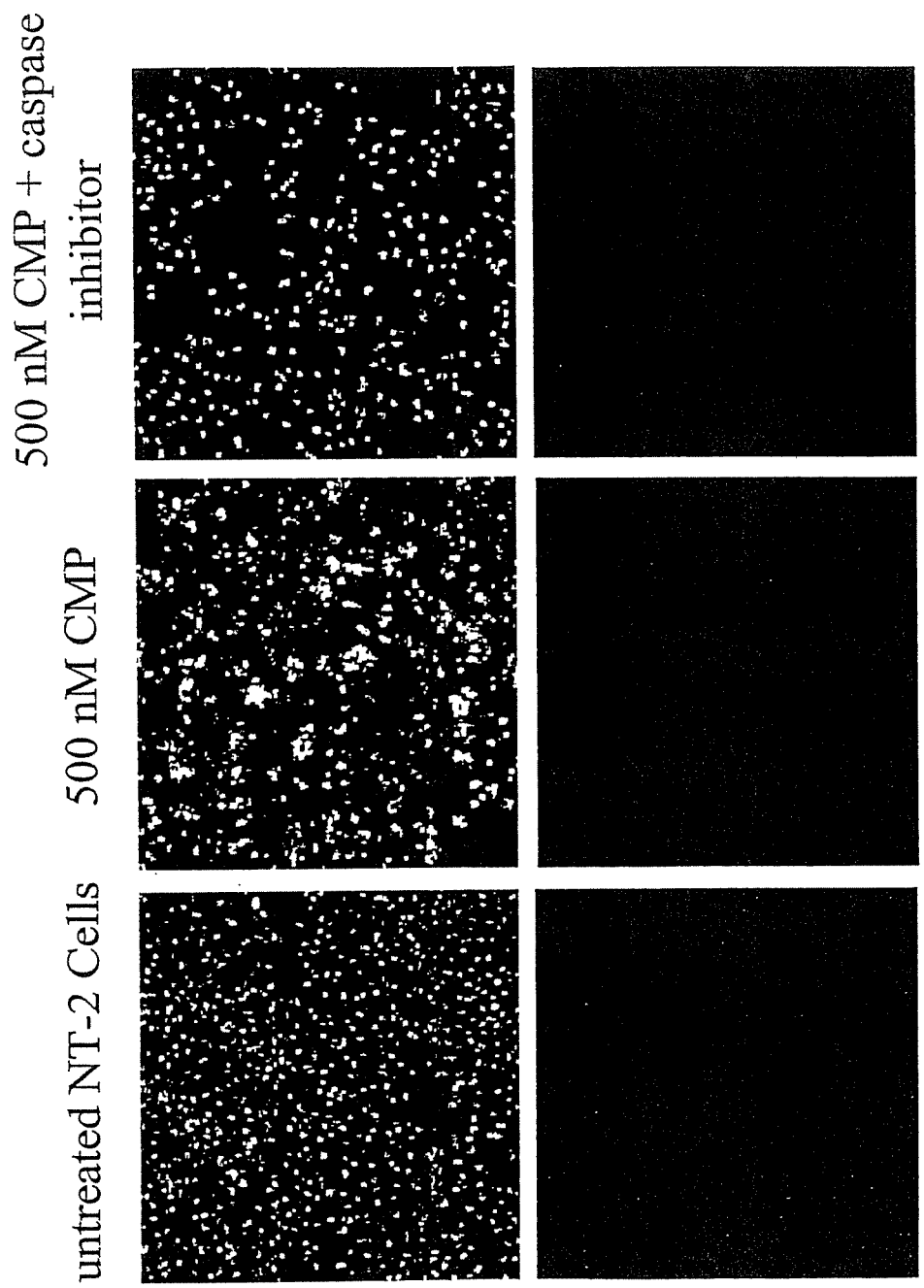

FIG. 9 shows image data from the FMAT 8100 System with grey scale (top) and two-color (bottom) images from representative wells containing peptide conjugate 9 and NT-2 cells; untreated (left); treated with 500 nM camptothecin (CMP) to induce apoptosis (middle); and 500 nM camptothecin, then caspase inhibitor DEVD-FMK (right). In the bottom panels, red cell images correspond to a channel 2/channel 1 fluorescence intensity ratio of >0.5 and blue cell images correspond to a channel 2/channel 1 fluorescence intensity ratio of <0.5. Channel 2 measures emission fluorescence from 685-720 nm and channel 1 measures emission fluorescence from 650-685 nm. The ratio of channel 2/channel 1 fluorescence intensity inversely correlates with the percentage of cells which are apoptotic.

Figure 10:
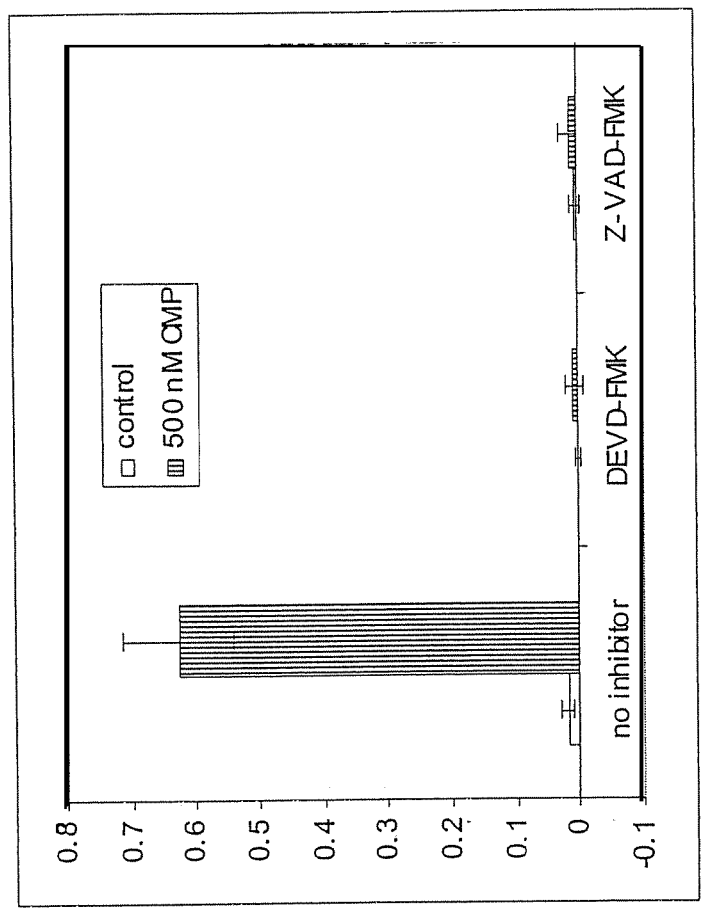

FIG. 10 shows quantitative results from the experiments of FIG. 9 with peptide conjugate 9 and NT-2 cells; with and without CMP to induce apoptosis; and with and without caspase inhibitors, Z-DEVD-FMK and Z-VAD-FMK.

Figure 11:
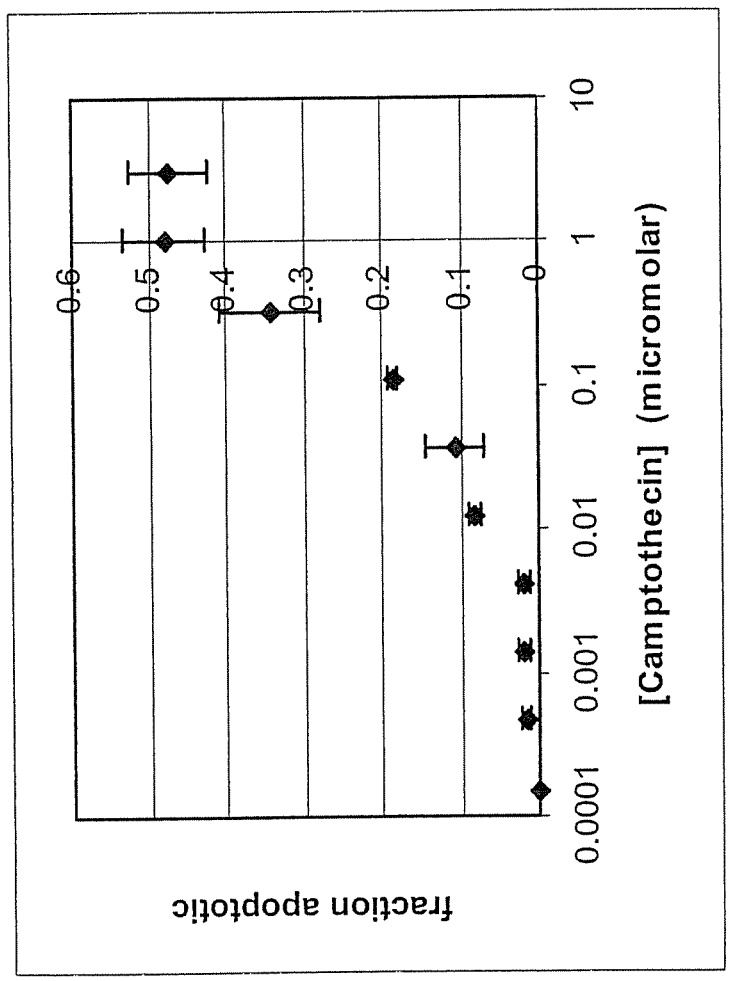

FIG. 11 shows ratiometric analysis by a plot of the fraction of apoptotic NT-2 cells as a function of camptothecin concentration (0.0001 to 10 µM) in the presence of peptide conjugate 9.

Figure 12:
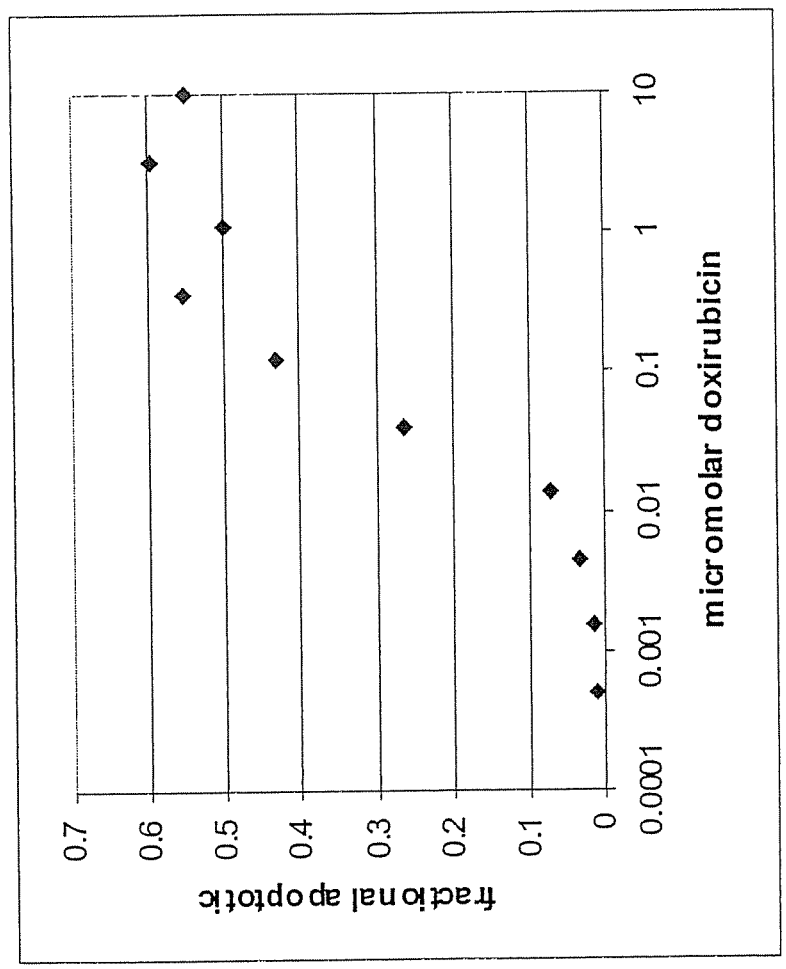

FIG. 12 shows ratiometric analysis by a plot of the fraction of apoptotic NT-2 cells as a function of doxirubicin concentration (0.0001 to 10 µM) induction of apoptosis in the presence of intracellular caspase substrate, peptide conjugate 9.

Figure 13:
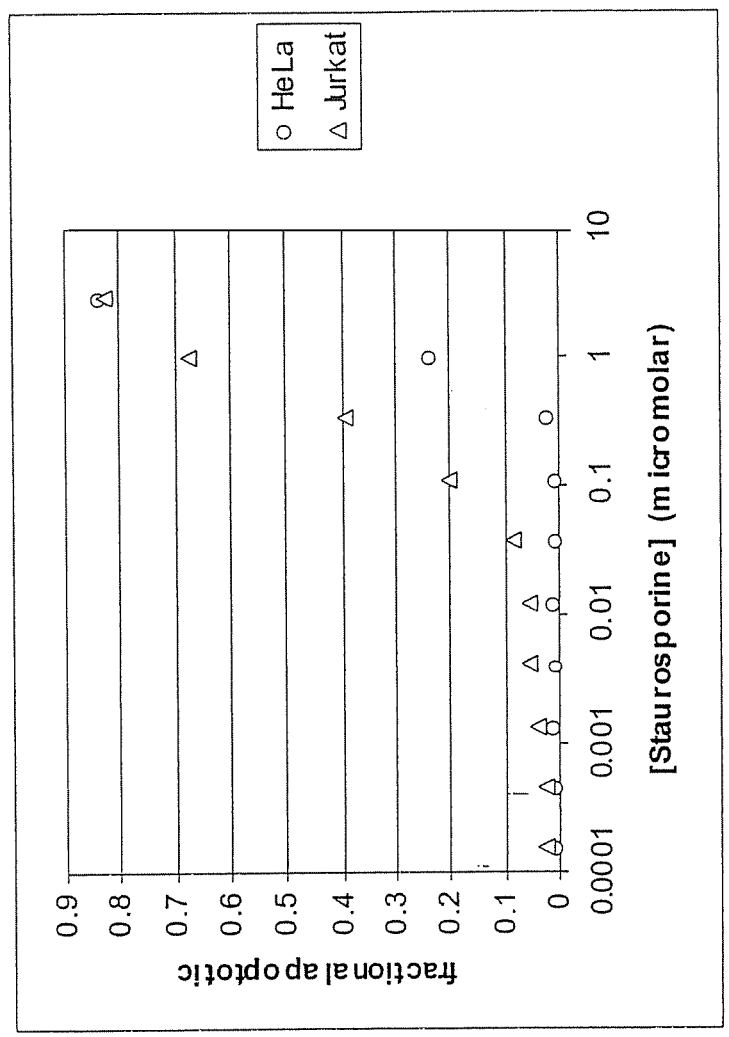

FIG. 13 shows a plot of the fraction of apoptotic HeLa (○) and Jurkat (Δ) cells as a function of staurosporine concentration (0.0001 to 10 µM) in the presence of peptide conjugate 9.

VI. DETAILED DESCRIPTION OF EXEMPLARY EMBODIMENTS

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

VI.1 DEFINITIONS

Unless stated otherwise, the following terms and phrases as used herein are intended to have the following meanings:

"Polypeptide", "protein" and "peptide" are polymers comprised of chains of amino acid monomers linked by amide or disulfide bonds. Polypeptides may be formed by a condensation reaction between the α-carbon carboxyl group of one amino acid and the amino group of another amino acid. Amino acids include the 20 or so that occur naturally and are gene-encoded, as well as analogs of amino acids. All of the amino acids used in the present invention may be either the D- or L-optical isomer. In addition, other peptidomimetics are also useful (Spatola, (1983) in *Chemistry and Biochemistry of Amino Acids, Peptides, and Proteins*, Weinstein, ed., Marcel Dekker, New York, p. 267). The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. An amino terminus may be modified or protected with a variety of functional groups or protecting groups. Similarly, the term "carboxy terminus" refers to the free carboxyl group on the carboxy terminus of a peptide or the carboxyl group of an amino acid at any other location within the peptide. A carboxy terminus may be modified, e.g. as an amide. The polypeptides described herein are written with the amino terminus at the left and the carboxyl terminus at the right, forming a sequence of amino acids.

"Amino acids" are represented interchangeably by their common names, their three letter code, or their one letter codes below:

| Amino Acid | Three letter | One letter |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid residues that are "conservative variants" or "conservative substitutions" for corresponding residues in a reference sequence are those that are physically or functionally similar to the corresponding reference residues, e.g. that have similar size, shape, electric charge, hydrophobicity, hydrophilicity, polarity, reactive chemical properties including the ability to form covalent or hydrogen bonds, and other properties. Particularly preferred conservative variants are those fulfilling the criteria defined for an "accepted point mutation" (Dayhoff et al, (1978) in *Atlas of Protein Sequence and Structure, Suppl.* 3, Natl. Biomed. Res. Foundation, Washington, D.C., chapter 22, pp. 352-54.). Conservative variants of amino acids typically include substitutions within the following groups: I. glycine, alanine, valine, isoleucine, leucine; II. aspartic acid, glutamic acid, asparagine, glutamine; III. serine, threonine; IV. lysine arginine; V. phenylalanine, tyrosine.

"Homologs" are peptides with substantially identical amino acid sequences which retain the lipid membrane-permeant function and which differ from the preferred sequences mainly or only by conservative amino acid substitutions, for example, substitution of one amino acid for another within the same class above, e.g. I. valine for glycine or IV. arginine for lysine) or by one or more non-conservative substitutions, deletions, or insertions located at positions of the amino acid sequence which do not destroy the function of the protein. Preferably, such a sequence is at least 85%, and more preferably 90%, and most preferably 95% identical at the amino acid level to the sequence of the peptide to which it is being compared.

A polypeptide includes an antibody or an enzyme. Polypeptides also include analogs and peptide mimetics such as amino acids joined by an ether as opposed to an amide bond. The constituent amino acids may be naturally occurring amino acids or structural analogs of natural amino acids that can function in a similar manner as naturally occurring amino acids. A peptide or protein analog comprises an unnatural or modified amino acid side-chain, a modified amide backbone, or modified terminus, e.g. carboxyl-terminus amide or cyclized polypeptide.

The terms "cleaving" or "cleavage" refer to breaking a covalent bond within a polypeptide. The term "cleavage site" thus refers to a particular amide peptide bond in a polypeptide which is cleaved by a protease enzyme, e.g. a caspase. Cleavage results in two polypeptide subunits.

The term "label", as used herein, means any moiety which can be attached to a polypeptide and that functions to: (i) provide a detectable signal; (ii) interact with a second label to modify the detectable signal provided by the first or second label; (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

The term "solid support" refers to any solid phase material upon which a polypeptide is synthesized. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, or a surface. Surfaces may be planar, substantially planar, or non-planar. Solid supports may be porous or non-porous, and may have swelling or non-swelling characteristics. A solid support may be configured in the form of a well, depression or other vessel. A plurality of solid supports may be configured in an array, addressable for robotic delivery of reagents, or by detection means including scanning by laser illumination and confocal or deflective light gathering.

The term "peptide conjugate" means a polypeptide labelled with the donor and acceptor dyes of the invention, I and II.

The terms "linker" and "linkage" are used interchangeably and mean a chemical moiety comprising a covalent bond or a chain of atoms that covalently attaches, or is attached to, a label to a polypeptide, one label to another, or a solid support to a polypeptide.

"Linking moiety" means a chemically reactive group, substituent or moiety, e.g. a nucleophile or electrophile, capable of reacting with another molecule to form a linkage by a covalent bond.

"Substituted" as used herein refers to a molecule wherein one or more hydrogen atoms are replaced with one or more non-hydrogen atoms, functional groups or moieties. By example, an unsubstituted nitrogen is —$NH_2$, while a substituted nitrogen is —$NHCH_3$. Exemplary substituents include but are not limited to halogen, e.g., fluorine and chlorine, ($C_1$-$C_8$) alkyl, sulfate, sulfonate, sulfone, amino, ammonium, amido, nitrile, nitro, lower alkoxy, phenoxy, aromatic, phenyl, polycyclic aromatic, heterocycle, water-solubilizing group, linkage, and linking moiety.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1 to 12 saturated and/or unsaturated carbons, including, but not limited to, methyl, ethyl, propyl, butyl, and the like.

"Alkylsulfonate" is —$(CH_2)_n$—$SO_3H$, and n is an integer from 1 to 6.

"Alkoxy" means —OR where R is ($C_1$-$C_6$) alkyl.

"Alkyldiyl" means a saturated or unsaturated, branched, straight chain or cyclic hydrocarbon radical of 1 to 20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

"Aryl" means a monovalent aromatic hydrocarbon radical of 6 to 20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Aryleno" means an aromatic ring fused at two contiguous aryl carbons of a compound, i.e. a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system results in a fused aromatic ring system, e.g. naphthalene. Typical aryleno groups include, but are not limited to: [1,2]benzeno, [1,2]naphthaleno and [2,3]naphthaleno.

"Aryldiyl" means an unsaturated cyclic or polycyclic hydrocarbon radical of 6-20 carbon atoms having a conjugated resonance electron system and at least two monovalent radical centers derived by the removal of two hydrogen atoms from two different carbon atoms of a parent aryl compound.

"Heterocycle" means any ring system having at least one non-carbon atom in a ring, e.g. nitrogen, oxygen, and sulfur. Heterocycles include, but are not limited to: pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

"Substituted alkyl", "substituted alkyldiyl", "substituted aryl" and "substituted aryldiyl" mean alkyl, alkyldiyl, aryl and aryldiyl respectively, in which one or more hydrogen atoms are each independently replaced with another substituent. Typical substituents include, but are not limited to, —X, —R, —OH, —OR, —SR, —SH, —$NH_2$, —NHR, —$NR_2$, —$^+NR_3$, —N=$NR_2$, —$CX_3$, —CN, —OCN, —SCN, —NCO, —NCS, —NO, —$NO_2$, —$N_2^+$, —$N_3$, —NHC(O)R, —C(O)R, —C(O)$NR_2$—S(O)$_2$O$^-$, —S(O)$_2$R, —OS(O)$_2$OR, —S(O)$_2$NR, —S(O)R, —OP(O)(OR)$_2$, —P(O)(OR)$_2$, —P(O)(O$^-$)$_2$, —P(O)(OH)$_2$, —C(O)R, —C(O)X, —C(S)R, —C(O)OR, —CO$_2^-$, —C(S)OR, —C(O)SR, —C(S)SR, —C(O)$NR_2$, —C(S)$NR_2$, —C(NR)$NR_2$, where each X is independently a halogen and each R is independently —H, $C_1$-$C_6$ alkyl, $C_5$-$C_{14}$ aryl, heterocycle, or linking group.

"Water-solubilizing group" means a substituent which increases the solubility of the compounds of the invention in aqueous solution. Exemplary water-solubilizing groups include but are not limited to quaternary amine, sulfate, sulfonate, carboxylate, phosphonate, phosphate, polyether, polyhydroxyl, and boronate.

"FRET" means fluorescent resonance energy transfer, a process by which two moieties, e.g. a donor dye and acceptor dye, interact. In a FRET assay of the invention, performed either in vivo or in vitro, the donor and acceptor are chosen for their spectral properties such that the excitation spectrum of the acceptor dye overlaps with the emission spectrum of the excited donor dye. The donor dye is excited by light of appropriate intensity within the donor's excitation spectrum. The donor then emits some of the absorbed energy as fluorescent light and dissipates some of the energy by FRET to the acceptor dye. The fluorescent energy it produces is quenched by the acceptor dye. FRET can be manifested as a reduction in the intensity of the fluorescent signal from the donor, reduction in the lifetime of its excited state, and re-emission of fluorescent light at the longer wavelength of the acceptor. When the donor and acceptor labels become spatially separated, e.g. by cleavage of a bond, FRET is diminished or eliminated.

"Array" means a predetermined spatial arrangement of polypeptides, cells, or other samples present on a solid support or in an arrangement of vessels, e.g. wells.

VI.2 POLYPEPTIDE SYNTHESIS

Polypeptides are prepared by automated synthesizers on a solid support (Perkin (1963) J. Am. Chem. Soc. 85:2149-54) by any of the known methods, e.g. Fmoc or BOC (Atherton (1981) J. Chem. Soc. 538-46). Activated amino acids are coupled onto a growing chain of amino acids, with appropriate coupling reagents. The polypeptides of the invention were synthesized with amino acid monomer units where the α-amino group was protected with Fmoc (fluorenylmethoxycarbonyl). Alternatively, the BOC method of peptide synthesis can be practiced to prepare the peptide conjugates of the invention.

Amino acids with reactive side-chains were further protected with appropriate protecting groups. Amino groups on lysine side-chains to be labelled with donor and acceptor labelling reagents of the invention were protected with the Dde protecting group, selectively removable with hydrazine-containing reagents. A large number of different protecting group strategies can be employed to efficiently prepare polypeptides which can be labelled with donor and acceptor label reagents. By appropriate selection of the protecting groups, reagents, and conditions, the peptide conjugates of the invention are accessible.

The solid support was either a polyethyleneoxy/polystyrene graft copolymer (TentaGel, Rapp Polymere GMBH, Tubingen, Germany) or a low-cross link, high-swelling Merrifield-type polystyrene with an acid-cleavable linker (Applied Biosystems). Polypeptides can be synthesized on other solid supports.

Polypeptides were synthesized on commercially available synthesizers at scales ranging from 3 to 50 μmoles. The Fmoc group was removed from the terminus of the peptide chain with a solution of piperidine in dimethylformamide (DMF), typically 30% piperidine, requiring several minutes for deprotection to be completed. The amino acid monomer, coupling agent, and activator was delivered into the synthesis chamber or column, with agitation by vortexing or shaking. Typically, the coupling agent was HBTU and activator was 1-hydroxybenzotriazole (HOBt). The coupling solution also contained diisopropylethylamine, or another organic base, to adjust the pH to an optimal level for rapid and efficient coupling.

Peptides may alternatively be prepared on chlorotrityl polystyrene resin by typical solid-phase peptide synthesis methods with a Model 433 Peptide Synthesizer (Applied Biosystems, Foster City, Calif.) and Fmoc/HBTU chemistry (Fields, (1990) Int. J. Peptide Protein Res. 35:161-214). The crude protected peptide on resin may be cleaved with 1% trifluoroacetic acid (TFA) in methylene chloride for about 10 minutes. The filtrate is immediately raised to pH 8 with an organic amine base, e.g. 4-dimethylaminopyridine. After evaporating the volatile reagents, a crude protected peptide is obtained and used directly to conjugate the acceptor and donor dyes of the invention.

One, both, or neither of the donor and acceptor labels can be coupled to the peptide while the peptide is still bound to the synthesis solid support. An exemplary synthetic route is to couple one of the label reagents to an unprotected side-chain nucleophile, e.g. a lysine amino, while the polypeptide is bound to the solid support and the N-terminus is Fmoc protected. The polypeptide may then be cleaved from the solid support and the N-terminus deprotected. The second label reagent may then be coupled to the polypeptide to complete the synthesis of a peptide conjugate bearing donor and acceptor dyes. This approach is illustrated in Example 3 and FIGS. 3-5.

Following synthesis, the peptide on the solid support (resin) is deprotected and cleaved from the support. Deprotection and cleavage may be performed in any order, depending on the protecting groups, the linkage between the peptide and the support, and the labelling strategy. After cleavage and deprotection, peptides may be desalted by gel filtration, precipitation, or other means, and analyzed. Typical analytical methods useful for the peptides and peptide conjugates of the invention include mass spectroscopy, absorption spectroscopy, HPLC, and Edman degradation sequencing. The peptides and peptide conjugates of the invention may be purified by reverse-phase HPLC, gel filtration, electrophoresis, or dialysis.

VI.3 DONOR AND ACCEPTOR LABELLING REAGENTS

Polypeptides may be conjugated, or "labelled", with labelling reagents to prepare the peptide conjugates of the invention. Peptides, proteins, antibodies, and other biopolymers comprised of amino acids and amino acid analogs may be covalently labelled by conjugation with the donor and acceptor (structures I and II) dyes of the invention. Typically, the dyes bear an electrophilic linking moiety which reacts with a nucleophilic group on the peptide, e.g. amino terminus, or side-chain nucleophile of an amino acid. Alternatively, the dye may be in nucleophilic form, e.g. amino- or thiol-linking moiety, which reacts with an electrophilic group on the peptide, e.g. NHS of the carboxyl terminus or carboxyl side-chain of an amino acid. The polypeptide may be on a solid support, i.e. synthesis resin, during the labelling reaction. Alternatively, the polypeptide may have been cleaved prior to labelling. Certain amino acid side-chains allow labelling with activated forms of the donor and acceptor dyes of the invention. Aspartic acid, glutamic acid, lysine, arginine, cysteine, histidine, and tyrosine have reactive functionality for labelling. By appropriate selection of protecting groups, certain reactive functionality on the peptide can be selectively unmasked for reaction with a labelling reagent.

Donor dye and acceptor dye labelling reagents of the invention include dibenzorhodamine structures I:

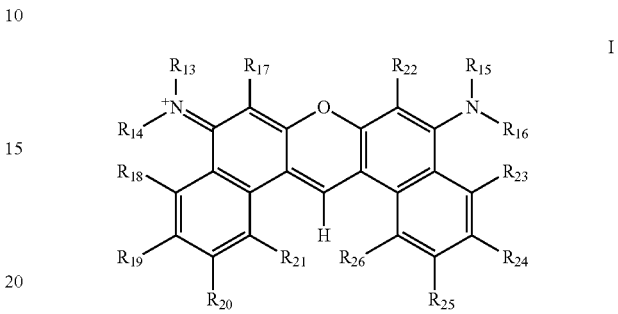

Label reagents I are substituted where $R_{13}$, $R_{14}$, $R_{15}$, and $R_{16}$ are selected from hydrogen, $C_1$-$C_{12}$ alkyl, $C_1$-$C_{12}$ alkyldiyl, phenyl, substituted phenyl, benzyl, substituted benzyl, biphenyl, substituted biphenyl, naphthyl, substituted naphthyl, heterocycle, substituted heterocycle, a water-solubilizing group and a linking moiety.

$R_{13}$, $R_{14}$, $R_{15}$, and $R_{16}$ may also include $C_1$-$C_6$ alkylsulfonate, $C_4$-$C_{10}$ arylsulfonate:

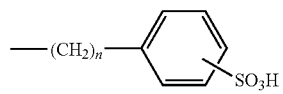

$C_1$-$C_6$ alkylcarboxylate, or $C_4$-$C_{10}$ arylcarboxylate:

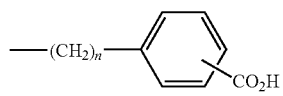

where n is 0 or 1.

$R_{13}$ when taken together with $R_{14}$ may be $C_2$-$C_8$ alkyldiyl; $R_{15}$ when taken together with $R_{16}$ may be $C_2$-$C_8$ alkyldiyl; $R_{13}$ when taken together with $R_{17}$ may be $C_2$-$C_8$ alkyldiyl; and $R_{15}$ when taken together with $R_{22}$ may be $C_2$-$C_8$ alkyldiyl. For example, dibenzorhodamine structures include Ia:

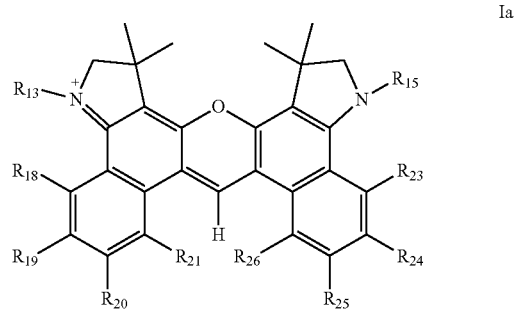

$R_{17}$, $R_{18}$, $R_{19}$, $R_{20}$, $R_{21}$, $R_{22}$, $R_{23}$, $R_{24}$, $R_{25}$, and $R_{26}$ are selected from hydrogen, fluorine, chlorine, bromine, $C_1$-$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), primary amino (—$NH_2$), ammonium (—$NH_3^+$), secondary amino (—NHR), tertiary amino (—$NR_2$), quaternary amine (—$NR_3^+$), amido (—$CONR_2$), nitrile (—CN), nitro (—$NO_2$), $C_1$-$C_8$ alkoxy (—OR), phenoxy, phenolic, tolyl, phenyl, $C_5$-$C_{10}$ aryl, benzyl, heterocycle, phosphonate, phosphate, sulfate, polyethyleneoxy, a water-solubilizing group, and a linking moiety. R may be $C_1$-$C_6$ alkyl, $C_1$-$C_6$ alkyldiyl. Ar may be $C_5$-$C_{14}$ aryl. At least one of $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, and $R_{26}$ is a linking moiety.

$R_{19}$ and $R_{20}$, when taken together, may be $C_5$-$C_{14}$ aryleno; and $R_{24}$ and $R_{25}$, when taken together, may be $C_5$-$C_{14}$ aryleno. For example, dibenzorhodamine structures include Ib and Ic:

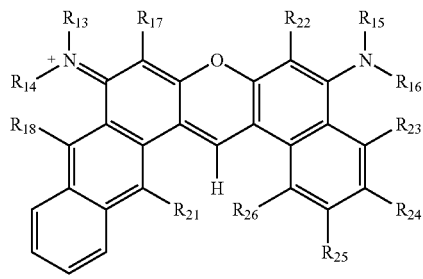

Ib

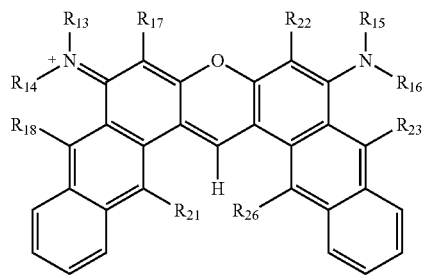

Ic

Donor dye and acceptor dye labelling reagents of the invention include diamino-benzophenoxazine structures II:

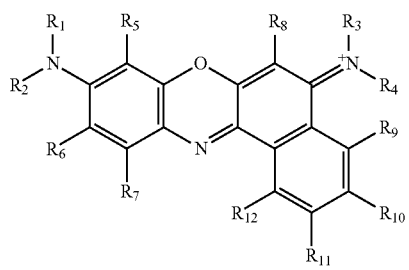

II

Label reagents II are substituted where $R_1$, $R_2$, $R_3$, and $R_4$ are selected from hydrogen, $C_1$-$C_{12}$ alkyl, $C_1$-$C_{12}$ alkyldiyl, phenyl, substituted phenyl, benzyl, substituted benzyl, biphenyl, substituted biphenyl, naphthyl, substituted naphthyl, heterocycle, substituted heterocycle, a water-solubilizing group, and a linking moiety.

$R_1$, $R_2$, $R_3$, and $R_4$ may also include amine and ammonium structures such as:
—$(CH_2)_n$—$NR_2$, —$(CH_2)_n$—$^+NR_3$, —$(CH_2)_n$—$^+NR_2$—$(CH_2)_n$—$NR_2$, and —$(CH_2)_n$—$^+NR_2$—$(CH_2)_n$—$^+NR_3$.
Each n is independently 2 or 3 and each R is independently selected from hydrogen, $C_1$-$C_6$ alkyl, $C_1$-$C_6$ alkyldiyl, and a linkage. Such amine and ammonium structures impart positive charges to the peptide conjugates.

$R_1$, $R_2$, $R_3$, and $R_4$ may also include $C_1$-$C_6$ alkylsulfonate, $C_4$-$C_{10}$ arylsulfonate:

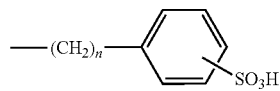

$C_1$-$C_6$ alkylcarboxylate, or $C_4$-$C_{10}$ arylcarboxylate:

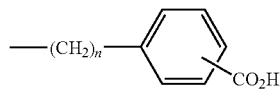

where n is 0 or 1.

$R_1$ when taken together with $R_2$ may be $C_2$-$C_8$ alkyldiyl; and $R_3$ when taken together with $R_4$ may be $C_2$-$C_8$ alkyldiyl.

$R_5$, $R_6$, $R_7$, $R_8$, $R_9$, $R_{10}$, $R_{11}$, and $R_{12}$ are selected from hydrogen, fluorine, chlorine, bromine, $C_1$-$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), primary amino (—$NH_2$), ammonium (—$NH_3^+$), secondary amino (—NHR), tertiary amino (—$NR_2$), quaternary amine (—$NR_3^+$), amido (—$CONR_2$), nitrile (—CN), nitro (—$NO_2$), $C_1$-$C_8$ alkoxy (—OR), phenoxy, phenolic, tolyl, phenyl, $C_5$-$C_{20}$ aryl, benzyl, heterocycle, phosphonate, phosphate, sulfate, polyethyleneoxy, a water-solubilizing group, and a linking moiety. R may be $C_1$-$C_6$ alkyl, $C_1$-$C_6$ alkyldiyl. Aryl groups (Ar) may be $C_5$-$C_{14}$ aryl. At least one of $R_1$, $R_2$, $R_3$, $R_4$, $R_5$, $R_6$, $R_7$, $R_8$, $R_9$, $R_{10}$, $R_{11}$, and $R_{12}$ is a linking moiety.

$R_6$ and $R_7$, when taken together, may be $C_5$-$C_{14}$ aryleno; and $R_{10}$ and $R_{11}$, when taken together, may be $C_5$-$C_{14}$ aryleno. For example, diamino-benzophenoxazine structures include IIa and Ib:

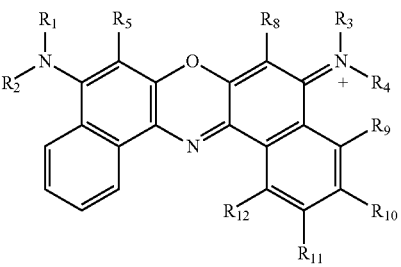

IIa

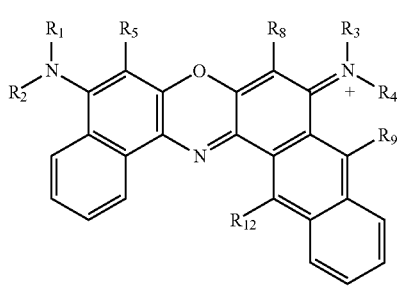

The dye label reagents include a reactive linking group, "linking moiety", at one of the substituent positions for covalent attachment of the dye to a polypeptide. Linking moieties capable of forming a covalent bond are typically electrophilic functional groups capable of reacting with nucleophilic molecules, such as alcohols, alkoxides, amines, hydroxylamines, and thiols. Examples of electrophilic linking moieties include succinimidyl ester, isothiocyanate, sulfonyl chloride, sulfonate ester, silyl halide, 2,6-dichlorotriazinyl, pentafluorophenyl ester, phosphoramidite, maleimide, iodoacetamide, haloacetyl, epoxide, alkylhalide, allyl halide, aldehyde, ketone, acylazide, and anhydride.

One linking moiety is an N-hydroxysuccinimidyl ester (NHS) of a carboxyl group substituent on an acceptor or donor dye of the invention. The NHS ester form of the dye is an exemplary labelling reagent. Donor and acceptor labelling reagents bearing the NHS group are exemplified by the structure:

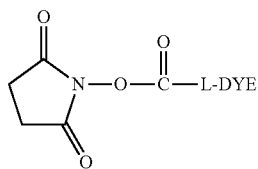

The linkage L may be a bond or $C_1$-$C_{12}$ alkyldiyl. DYE is a donor or an acceptor dye of the structures I and II.

The activated ester, e.g. NHS or HOBt, of the dye may be preformed, isolated, purified, and/or characterized, or it may be formed in situ and reacted with a nucleophilic group of a polypeptide. Typically, the carboxyl form of the dye is activated by reacting with some combination of: (1) a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate); (2) an activator, such as 1-hydroxybenzotriazole (HOBt) or 1-hydroxyazabenotriazole (HOAt); and (3) N-hydroxysuccinimide to give the NHS ester of the dye. See Examples 1 and 2. Exemplary substituent positions for NHS esters on structures I are $R_{13}$, $R_{14}$, $R_{15}$ and $R_{16}$. Exemplary substituent positions for NHS esters on structures II are $R_1$, $R_2$, $R_3$ and $R_4$. Representative examples of NHS esters of a dibenzorhodamine and a diamino-benzophenoxazine are structures 2 and 4 in Examples 1 and 2, respectively.

Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and arylsulfonyl halides, e.g. triisopropylbenzenesulfonyl chloride.

Another preferred linking moiety is a phosphoramidite reagent of the acceptor and donor dyes of the present invention. Phosphoramidite dye reagents are particularly useful for labelling of polypeptides by automated synthesis on solid support. Oligonucleotides are commonly synthesized on solid supports by the phosphoramidite method (Caruthers, U.S. Pat. No. 4,415,732; Caruthers, U.S. Pat. No. 4,458,066; Beaucage (1992) Tetrahedron 48:2223-2311).

Phosphoramidite dye reagents have the general formula:

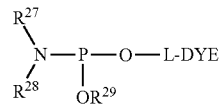

where DYE is a protected or unprotected form of an acceptor or donor dye, i.e. structures I or II. L is a linker. $R^{27}$ and $R^{28}$ taken separately are $C_1$-$C_{12}$ alkyl, $C_4$-$C_{10}$aryl, and cycloalkyl containing up to 10 carbon atoms, or $R^{27}$ and $R^{28}$ taken together are $C_2$-$C_8$ alkyldiyl, forming a saturated nitrogen heterocycle with the phosphoramidite nitrogen atom. $R^{29}$ is a phosphite ester protecting group which prevents unwanted extension of the oligonucleotide. Generally, $R^{29}$ is stable to the coupling conditions yet is able to be removed from peptide conjugate product with a reagent that does not adversely affect the integrity of the polypeptide or the dye. Preferably, $R^{29}$ is: (i) methyl, (ii) 2-cyanoethyl; —CH$_2$CH$_2$CN, or (iii) 2-(4-nitrophenyl)ethyl; —CH$_2$CH$_2$(p-NO$_2$Ph). Preferred embodiments of phosphoramidite reagents are where: (i) $R^{27}$ and $R^{28}$ are each isopropyl, or when $R^{27}$ and $R^{28}$ taken together is morpholino, (ii) L is $C_1$-$C_{12}$ alkyl, (iii) $R^{29}$ is 2-cyanoethyl, and (iv) DYE is attached by a linker. Phosphoramidite dye reagents effect labelling of a polypeptide with a single acceptor or donor dye of the invention at the amino terminus of the polypeptide, as a consequence of the carboxyl to amino directionality of peptide synthesis. Phosphoramidite dye reagents allow for labelling at other sites of an polypeptide, e.g. an amino acid side-chain nucleophile such as the amino of lysine, the hydroxyl of serine, threonine, and tyrosine, or the thiol of cysteine. Labelling at the amino acid side-chains allows for internal and multiple labelling of the polypeptide with acceptor and donor dyes of the invention.

VI.4 POLYPEPTIDE CONJUGATES

Peptide conjugates of the invention are labelled with two dye moieties: a donor dye and a acceptor dye, selected from dibenzorhodamine structures I and diamino-benzophenoxazine structures II. The donor and acceptor of a peptide conjugate may be any combination of two dibenzorhodamines, two diamino-benzophenoxazines, or one of each. In other words, the donor may be either a dibenzorhodamine or a diamino-benzophenoxazine. Likewise, the acceptor may be either a dibenzorhodamine or a diamino-benzophenoxazine. The dyes provide a detection element for localizing, visualizing, and quantitating the cleavage event. The properties of the dyes also facilitate transport through the cell membrane and targeting of intracellular structures and molecules. The donor and acceptor of any particular peptide conjugate are selected as a pair to match their spectral properties. In particular, their spectral overlap which allows fluorescence resonance energy transfer (FRET) to occur. The donor may be partially or significantly quenched by the acceptor in an intact peptide. Upon cleavage of the peptide by a peptidase or protease, such as a caspase, a detectable increase in fluorescence from the donor may be measured (Knight, C. (1995) "Fluorimetric Assays of Proteolytic Enzymes", Methods in Enzymology, Academic Press, 248:18-34). In addition, fluorescent emissions from the acceptor dye may be also detected, quantitated, and/or localized inside or outside the cell. The peptide conjugates of the invention retain the specific binding and recognition properties of the respective dyes and peptide sequence.

Figure 1:
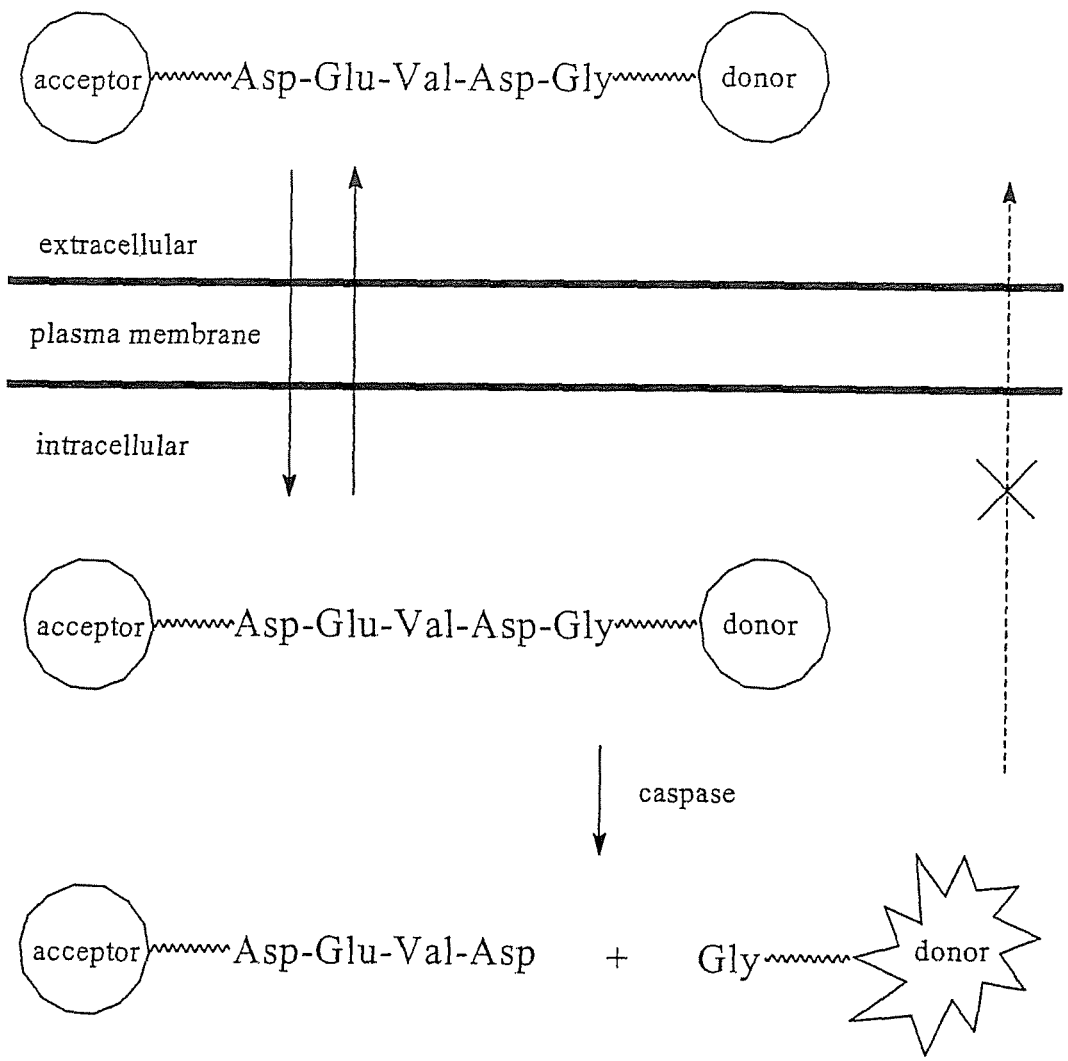
FIG. 1 shows a schematic of the passage of a peptide conjugate comprising the DEVDG amino acid sequence and donor and acceptor dyes across the plasma membrane of a cell and cleavage of the peptide conjugate by caspase.

Certain polypeptide sequences of peptide conjugates are substrates for caspase enzymes. In particular, the sequences Asp-Glu-Val-Asp (DEVD) (SEQ ID NO: 1), Asp-Glu-Val-Asp-Gly (DEVDG) (SEQ ID NO: 3) and Gly-Asp-Glu-Val-Asp-Gly-Ile-Lys (GDEVDGIK) (SEQ ID NO: 2) are caspase-specific sequences which result in cleavage by caspase of an amide bond in the peptide conjugate (FIG. 1). The DEVDG sequence in the peptide conjugate represented below may be flanked by other amino acids where n may be 0 to 100.

the carboxy terminus. Polypeptides can be functionalized to bear reactive amino, thiol, sulfide, disulfide, hydroxyl, and carboxyl groups at any of these sites.

Labelling can be accomplished using any one of a large number of known techniques, methods, standard reagents and reaction conditions. A general protocol for conjugating the dyes in the NHS ester form to peptides with an N-terminus amino group or a nucleophilic amino acid side-chain, e.g. cysteine or lysine, entails dissolving the NHS esters in aqueous acetonitrile (the percentage of acetonitrile is determined by the hydrophobicity of the dye to attain solubility) with peptides in water (or aqueous acetonitrile solution if peptides were hydrophobic). Aqueous sodium bicarbonate buffer (1 M) is added to the solution to achieve 0.1M buffer concentration while vortexing or shaking. The mixture is shaken at room temperature for 10 minutes to 30 minutes. The crude peptide-dye conjugate in the reaction mixture can be directly purified by reverse-phase HPLC.

In one method for labelling polypeptides, a nucleophilic functionality, e.g. a primary aliphatic amine, is introduced at a labelling attachment site on an polypeptide, e.g. an amino terminus. After automated, solid-support synthesis is complete, the polypeptide is cleaved from the support and all protecting groups are removed. The nucleophile-polypeptide is reacted with an excess of a label reagent containing an electrophilic linking moiety, e.g. isothiocyanate or activated

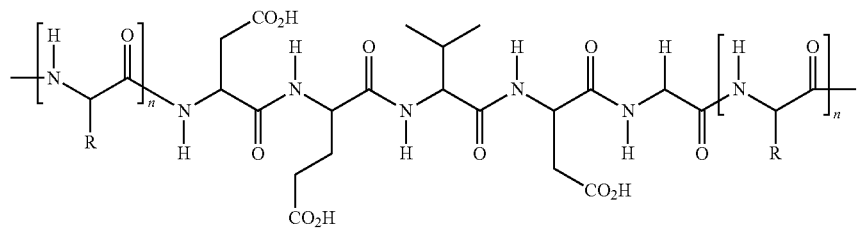

Figure 2:
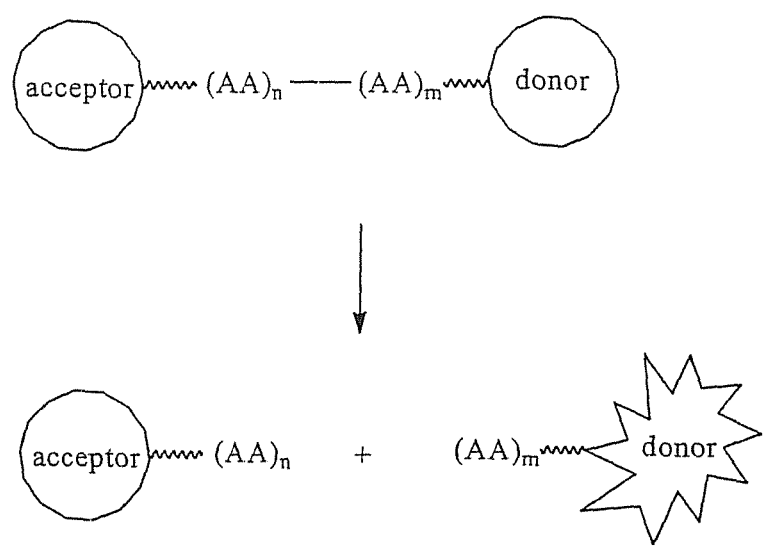
FIG. 2 shows the general structure of a peptide conjugate comprised of a sequence of amino acids (AA), a donor dye, and an acceptor dye. Cleavage of a peptide bond separates the peptide into two fragments; a fragment bearing n amino acids and the acceptor dye, and a fragment bearing m amino acids and the donor dye.

A protease binding site is an amino acid sequence (polypeptide) which is recognized and cleaved by a particular protease (Komoriya, U.S. Pat. No. 5,714,342). The polypeptides of the invention are substrates for the family of caspase enzymes. Caspases are known to cleave polypeptide substrates adjacent to particular amino acids within a recognition site. A particular caspase does not cleave every bond in a substrate that has any particular amino acid. Rather, caspases are specific to particular amino acid sequences which serve as recognition domains for each particular caspase. Any polypeptide that comprises the DEVD caspase recognition site can be a peptide conjugate of the invention. In this recognition site, the cleavage site is the amide bond between the aspartic acid residue D toward the carboxyl terminus and the adjacent amino acid. For example, the caspase recognition site in a peptide containing the sequence $(AA)_n$-DEVDG-$(AA)_m$ will cleave to form $(AA)_n$-DEVD and G-$(AA)_m$ peptide fragments, the former with a D carboxy-terminus and the latter with a G amino-terminus. See FIGS. 1 and 5 for a specific example, and FIG. 2 for a general example.

The donor dye and acceptor dye moieties are covalently attached by linkages to the polypeptide. Rigid and non-rigid linkages may be useful. Generally, the linkage linking the label and the polypeptide should not (i) inhibit membrane permeability, (ii) inhibit enzymatic activity, or (iii) adversely affect the properties of the label, e.g. quenching or bleaching fluorescence of a dye. Polypeptides can be labelled at sites including an amino acid side-chain, the amino terminus, and ester, e.g. N-hydroxysuccinimide (NHS), under homogeneous solution conditions (Hermanson, *Bioconjugate Techniques*, (1996) Academic Press, San Diego, Calif. pp. 40-55, 643-71).

As an example, the terminal amine of lysine can be protected with a Dde group while the N-terminal backbone amine is protected with Fmoc (fluorenylmethoxycarbonyl). After synthesis of the peptide is complete, the Dde is selectively removed with hydrazine while the Fmoc group stays intact. One or more lysine amino groups are thus available for labelling with a first electrophilic dye reagent such as an NHS ester. The peptide may be further manipulated, e.g. cleaved, deprotected, or purified. The N-terminal Fmoc group may then be removed and the resulting N-terminal amino group reacted with a second and different dye reagent. Other protecting groups, other sites on the peptide, and other sequences of steps are available to one skilled in the art of labelling peptides to specifically prepare peptide conjugates labelled at designed sites with the donor and acceptor dyes of the invention.

In some cases, the dyes and the polypeptide may be coupled by in situ activation of the dye and reaction with the polypeptide to label the polypeptide in one step. For example, the carboxyl group of a donor or acceptor dye may be activated and coupled with an N-terminus or side-chain amino group of a peptide to give a labelled polypeptide in one vessel. Alternatively, the terminal carboxyl or side-chain carboxyl of a peptide may be activated and coupled with an amino group a donor or acceptor dye to give a labelled polypeptide. A useful activator and coupling reagent is BOP (Benzotriazol-1-yloxy-tris(dimethyl-amino)phosphonium hexafluorophosphate). As an example, about 1 mg of a crude protected peptide with a free carboxyl terminus is dissolved in dimethylformamide (DMF) or acetonitrile and mixed with a molar excess of BOP and a donor or acceptor dye with an amino group, e.g. as a TFA salt. The mixture is shaken, stirred or let stand at room temperature for a few hours or a few days to couple the carboxyl terminus of the peptide to amino group of the dye to form an amide bond to make a dye labelled peptide conjugate. The solvent is completely removed, and the residue is deprotected with 30% TFA in methylene chloride for about 30 minutes. After evaporation, the mixture is purified by reverse-phased HPLC to give the dye labelled peptide conjugate.

In a second method, a label is directly incorporated into the polypeptide during or prior to automated synthesis, for example as a solid support reagent (U.S. Pat. Nos. 5,736,626 and 5,141,813) or as a modified amino acid.

Figure 3:
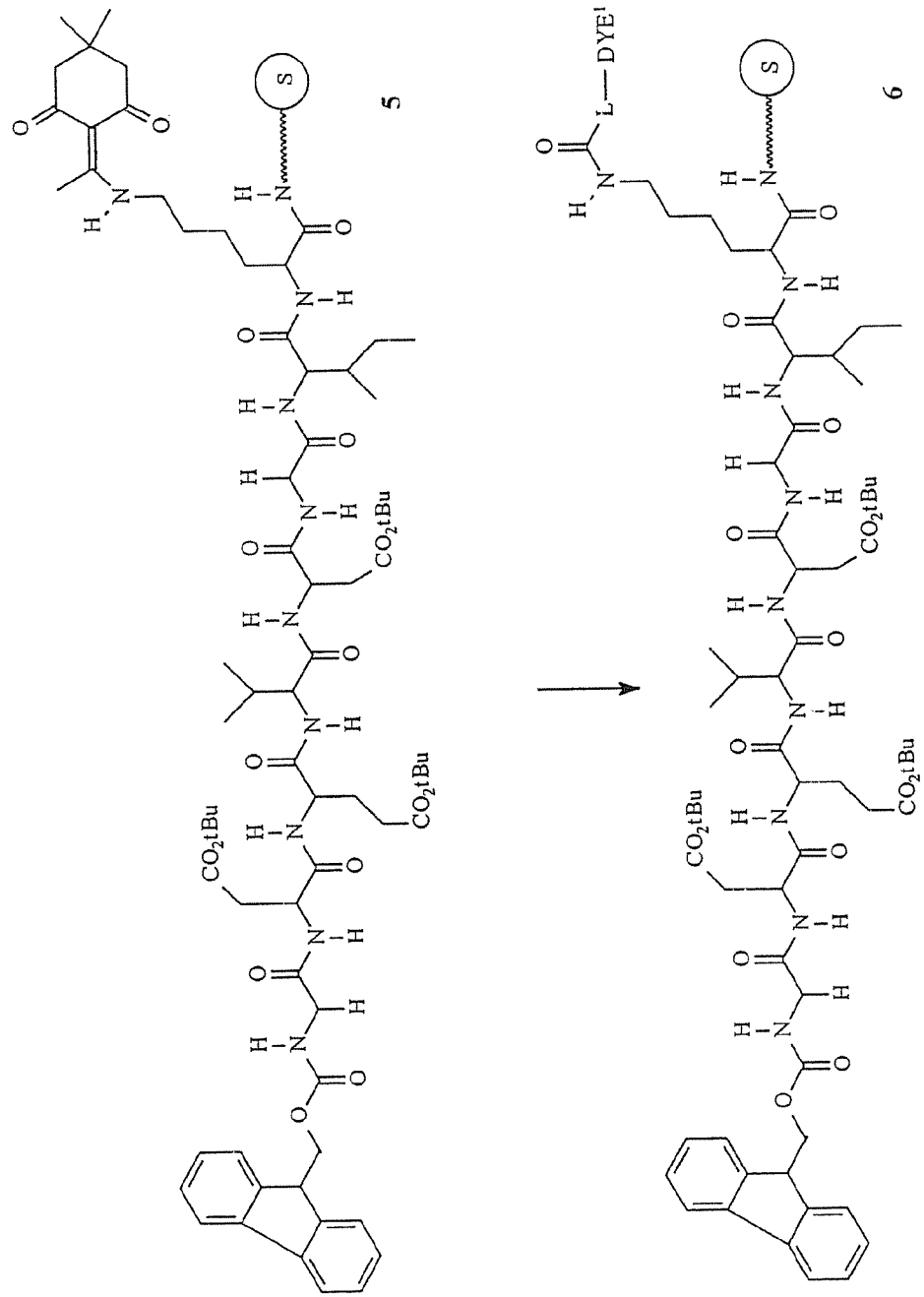
FIG. 3 shows deprotection of protected peptide on solid support 5 and coupling of the lysine amino to dye-NHS 2 to give mono-labelled peptide on solid support 6.
Figure 4:
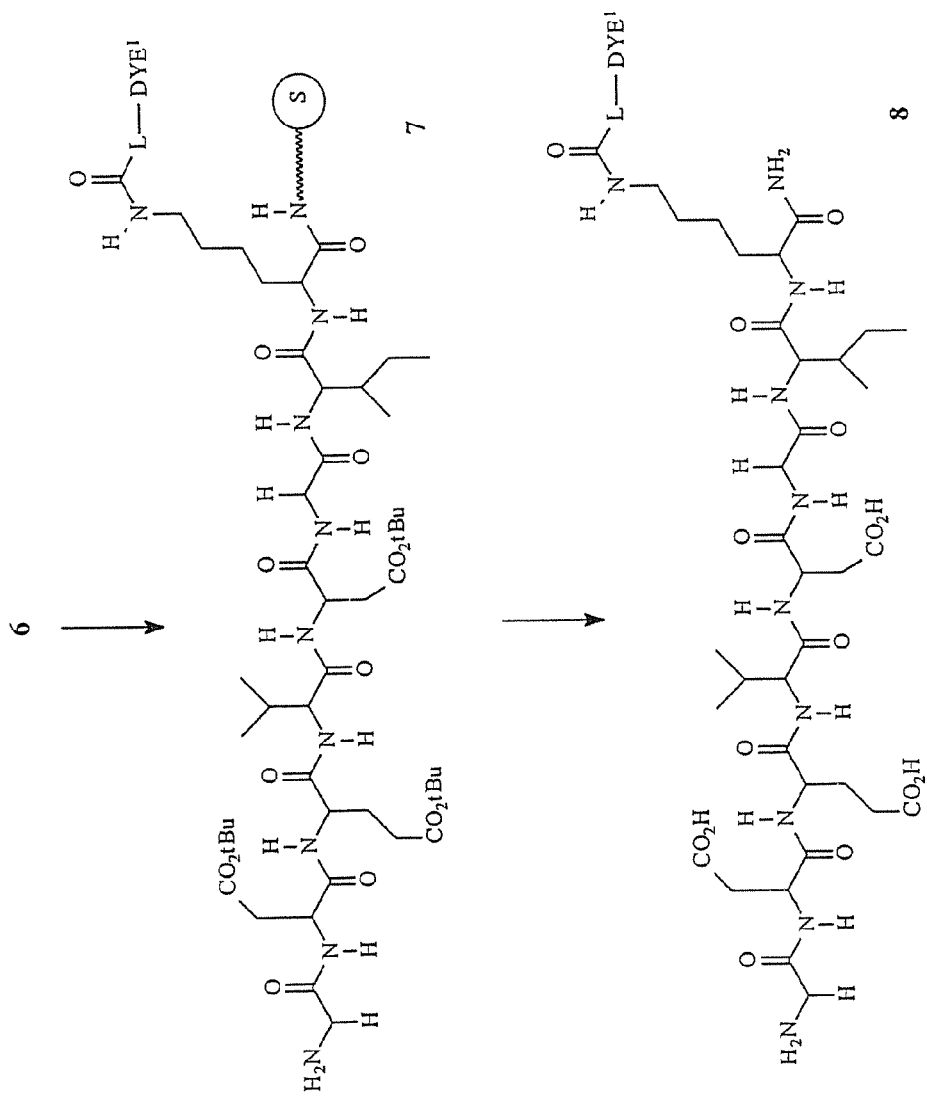
FIG. 4 shows removal of the N-terminus Fmoc protecting group of 6 to give mono-labelled peptide on solid support 7, and cleavage and deprotection give deprotected mono-labelled peptide 8.

In one example of the synthesis of a peptide conjugate substrate for caspase cleavage, protected peptide 5 on polystyrene support resin is synthesized on an automated peptide synthesizer (Example 3). The N-terminus is left protected with the Fmoc group and the side chain carboxyl groups of the glutamic acid and aspartic acid are protected as tert-butyl esters (FIG. 3). The Dde group of lysine is selectively removed with hydrazine and the lysine amino group is reacted with the NHS ester of dibenzorhodamine 2 (Example 1) to give 6. The Fmoc group is removed with piperidine to give 7 which is treated with aqueous TFA and thioanisole scavenger to remove the tert-butyl groups and cleave the linker to the resin to give the mono-labelled, deprotected peptide 8 (FIG. 4). The N-terminus is coupled with the NHS ester of diamino-benzophenoxazine 4 (Example 2) to give peptide conjugate 9 (FIG. 5a).

A surprising and unexpected aspect of the invention is that the donor dyes and the acceptor dyes selected from structures I and II undergo efficient energy-transfer when covalently attached as labels to a polypeptide. Prior to cleavage, the emissions of the donor dye are substantially quenched by energy transfer to the acceptor dye. The peptide conjugates of the invention may be designed such that upon cleavage the donor and acceptor dyes are separated, each attached to the resulting fragments. Intramolecular energy transfer by FRET or other means ceases. The donor and acceptor dyes may then be detected and spectrally resolved, e.g. by dual channel detection. A surprising and unexpected result is that the resulting labelled peptide fragments are substantially retained inside the cell, enabling cell counting and quantification of caspase activity by measurements of fluorescence intensity.

The absorbance spectrum of an acceptor dye overlaps with the emission spectrum of a proximal intramolecular or intermolecular donor dye such that the fluorescence of the donor dye is substantially diminished, or quenched, a phenomenon often referred to as fluorescence resonance energy transfer "FRET" (Clegg (1992) "Fluorescence resonance energy transfer and nucleic acids", Meth. Enzymol. 211:353-388). FRET is used to detect the assembly, dissociation or conformational rearrangement of protein and nucleic acid complexes (Ha (1999) Proc. Natl. Acad. Sci. USA 96:9077-82). An example of FRET in the present invention is where the polypeptide is labelled with a fluorescent donor dye and an acceptor dye. Acceptor dyes may or may not be fluorescent themselves. Fluorescent acceptor dyes allow for ratio analysis of fluorescence from the donor and acceptor dyes by two-channel detection. In some applications, non-fluorescent acceptor dyes may be advantageous because they eliminate background fluorescence that results from direct acceptor excitation.

Light, e.g. from a laser, at a first wavelength is absorbed by a donor dye. The donor dye emits excitation energy absorbed by an acceptor dye. Specific donor and acceptor dyes are selected together as a pair with consideration for spectral properties. Spectral overlap between the emission spectra of the donor dye and the excitation spectra of the acceptor dye may confer efficient energy transfer and quenching of the donor dye in the intact peptide conjugate. For example, the emission maximum (652 nm) of the dibenzorhodamine donor dye in 9 matches well with the excitation maximum (655 nm) of the diamino-benzophenoxazine acceptor dye. The acceptor dye fluoresces at a second, longer wavelength. For some applications, donor and acceptor dyes are referred to as reporter and quencher, respectively.

Those of skill in the art will appreciate that many of the peptide conjugates, including the donor and acceptor dye moieties may exhibit the phenomena of tautomerism, conformational isomerism, geometric isomerism and/or stereo isomerism. As the formulae drawings within this specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein.

In addition, it will also be apparent that the peptide conjugates of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state. Any and all protonated forms of the peptide conjugates are intended to fall within the scope of the invention.

Furthermore, the peptide conjugates of the invention may bear multiple positive or negative charges. The associated counter ions with the peptide conjugates are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion.

VI.5 ANALYSIS AND PURIFICATION OF PEPTIDE CONJUGATES

Labelled peptides are analyzed and purified by standard methods (Hermanson, *Bioconjugate Techniques*, (1996) Academic Press, San Diego, Calif. pp. 40-55, 643-71), including separation of the peptide conjugate from any unconjugated starting materials or unwanted by-products. The peptide conjugates can be stored dry or in solution for later use.

VI.6 IN VITRO CLEAVAGE OF PEPTIDE CONJUGATE 9 BY CASPASE-3

The excitation and emission spectra of peptide conjugate 9 (FIG. 5a) was measured in buffer (Example 5). Virtually no fluorescence excitation (FIG. 6) from the donor dye or emission (FIG. 7) from the acceptor dye is detected, indicating 9 is intact and no proteolytic cleavage has occurred. The arrows in FIG. 6 and FIG. 7 for 9 points to the baseline due to its almost complete lack of fluorescence due to quenching. Other peptide conjugates, i.e. different amino acid sequences and different donor and acceptor dyes, may show significant fluorescence when intact. However, when the donor and acceptor are matched to allow FRET, fluorescence will increase upon cleavage. When purified caspase-3 is added to 9, significant excitation fluorescence (FIG. 6) and significant emission fluorescence is detected (FIG. 7) from the donor dibenzorhodamine dye (DYE[1], FIG. 5b). The excitation and emission fluorescence after the addition of caspase-3 is deduced to derive from the peptide fragments 10 and 11 (FIG. 5a). Cleavage at the caspase recognition site of 9 leads to the loss of energy-transfer between the donor and acceptor dyes when they separate into fragments 10 and 11. The fluorescence intensity was monitored continuously after mixing peptide conjugate 9 with purified caspase-3 (FIG. 8). Emission from the donor dye increased rapidly during the first 5 to 10 minutes and stabilized in about an hour, indicating rapid cleavage.

Caspase-3 is just one of a family of caspase enzymes (Cysteine-dependent, aspartate-directed proteases) which may be used for in vitro cleavage of the peptide conjugates of the invention. Purified caspase enzymes are available commercially, as well as directions, protocols for their use, and assay kits (Sigma, St. Louis, Mo.; Intergen, Purchase, N.Y.). Peptide caspase substrates and inhibitors are also commercially available (Bachem Bioscience Inc., King of Prussia, Pa.; Calbiochem, San Diego, Calif.).

VI.7 CELL PREPARATION FOR CASPASE ASSAY

The methods of the invention employ standard tissue culture techniques including tissue culture medium comprising RPMI 1640 with 10% FBS fetal bovine serum. Human cell lines which were assayed for caspase activity included NT2, HeLa, and Jurkat cultures. In theory, any mammalian cells can be assayed by the methods disclosed herein, including monkey, rat and mice. Non-mammalian cells may serve as useful models, as long as the peptide conjugate-caspase specificity is conserved.

VI.8 DELIVERING PEPTIDE CONJUGATES INTO CELLS

Delivery of polypeptides into live cells is often challenging. Mechanical means such as microinjection and electroporation can kill or injure cells. A surprising and unexpected aspect of the invention is that polypeptides labelled with dibenzorhodamine donor dyes I and diamino-benzophenoxazine acceptor dyes II enter live cells efficiently, without damaging the cells. Another surprising and unexpected aspect of the invention is that apoptotic cells can be identified by the increase in fluorescence from the cells. Another surprising and unexpected aspect of the invention is that non-apoptotic cells can be identified by the absence of increased fluorescence. Another surprising and unexpected aspect of the invention is that after cleavage of a peptide conjugate of the invention, the cleaved peptide fragment bearing the diamino-benzophenoxazine acceptor dye II remains in the cell and binds to nucleic acid. The peptide conjugates of the invention readily diffuse into eukaryotic cells by the excellent membrane permeability properties conferred by the dyes. Diamino-benzophenoxazine dyes with cationic substituents are known to be effective as staining dyes, and undergo large quantum yield increases in association with nucleic acids (Yan, U.S. Pat. No. 6,140,500). Cell membrane permeability of the peptide conjugates may be further enhanced by incorporation of certain amino acid sequences which encode for fusion proteins, e.g. the lysine, arginine-rich GP32 sequences; transportan (Langel, U.S. Pat. No. 6,025,140); attennapedia proteins; and transduction peptides, e.g. TAT. The peptide conjugates may be loaded into vesicles to fuse with cell membranes.

One method for introducing the peptide conjugates into cells to induce apoptosis and measure caspase activity includes the following steps:
1. Plate the eukaryotic cells in RPMI 1640 media in the wells of a tissue culture-treated 96-well plate at 37° C. The cells will adhere to well bottoms in 1 to 24 hours. Any number of different sample cells or any combination of cells, inhibitors or apoptosis inducers can be assayed. Typically 10,000 cells per well are plated in about 100 µl of tissue culture media.
2. Add an apoptosis inducer, e.g. camptothecin or staurosporine, dissolved in media and/or solvent. Different concentrations can be used to study dose-response.
3. Let the cells stand for about 24 hours at 37° C., depending on the inducer.
4. Add the peptide conjugate, dissolved in media and/or solvent in a range of 1 to 10 µM, e.g. 2.5 µM, to every well, including controls. Let stand for about 90 minutes at 37° C.
5. Transfer plates to a fluorescent plate reading device, cell sorter, flow cytometer, laser imager, microscope, or other device and read the content of the wells.

The above method is conducive to high-throughput screening methods of intracellular assay, in part because only a single end-point fluorescence measurement is required. Alternatively, the peptide conjugate may be added before the apoptosis inducer. A time course study could thus be conducted, from t=0 to an hour or more, by measuring the increase in fluorescence intensity over time to show the effectiveness of an inducer.

VI.9 DETECTING AND QUANTITATING INTRACELLULAR CASPASE ACTIVITY WITH PEPTIDE CONJUGATES

Direct detection and quantification of intracellular fluorescence intensity and enumeration of fluorescently labelled events, such as caspase cleavage of the peptide conjugates of the invention, can be conducted on the FMAT™ 8100 HTS System (Applied Biosystems, Foster City, Calif.). The FMAT 8100 HIS System is a fluorescence macro-confocal, high-throughput screening instrument that automates detection of mix-and-read, non-radioactive assays with live cells or beads (Miraglia, J. Biomol. Screening (1999), 4(4) 193-204).

The FMAT 8100 system incorporates a laser scanner, optical detection, and analysis software for enumerating fluorescent changes in cells by emission detection in two channels. The macroconfocal optics enables detection in the red spectral region, minimizing any background fluorescence traditionally encountered using blue-green laser systems that can cause high autofluorescence from plate cells or screening compounds (Manian, U.S. Pat. Nos. 6,130,7455 and 6,181, 413). The system accommodates plates of multiple densities and is configured to read 96- and 384-well microtiter plates.

The scanning laser/detector head moves along the x, y, and z coordinates in increments as small as 4 microns. The laser excites the donor and acceptor dyes with light coming in from the bottom of each well. Fluorescence emissions are captured and stored as digitized image data, with the majority of background fluorescence subtracted. A one mm$^2$ image of each well is created, with up to 250 pixels. Beads or cell sizes can be measured from the images. The limit of resolution in object detection is about 5 microns. The electronic images are characterized by the analysis software on the basis of size, fluorescence intensity, mean fluorescence, and color. From the scanned fluorescent data, the location, shape and morphology of the cells are reconstructed in the digital format.

The FMAT 8100 system can differentiate between background fluorescence and fluorescence associated with cells or beads allowing for reliable and easy mix-and-read assays. Intermediate purification steps to remove excess label reagents or other fluorescent sources are typically obviated. The optics detect only the cells, or beads, which settle to the bottom of the vessel, e.g. well. The laser scans a 1 mm² area in one second with a depth of focus of approximately 100 μm from the bottom of the microwell plate. The light source is a 18 mW 633 nm red helium-neon scanning laser with a 8 μm diameter Gaussian spot. Total scan time for a 96 well plate is about 6 minutes, and about 15 minutes for a 384 well plate, although the scan rate could be more or less depending on the application and sample. The plate is made of polystyrene, but may be fabricated of other polymeric materials such as polycarbonate, polyacrylate, polymethacrylate, polyethylene, or polypropylene. Cells tend to settle to the bottom, or near the bottom, of the well or vessel. The laser light is cone-shaped in the detection range and auto-focused at each well location. An objective lens collects emission epifluorescence and passes it through a series of filters. A dichroic filter then splits the signal to two photomultiplier tubes (PMT). One collects light between 650-685 (channel 1); the other from 685-720 nm (channel 2) thus enabling two-color confocal detection in the far red region.

Alternatively, the methods of the invention may be conducted with a fluorescence microscope. The location and intensity of fluorescence derived from the peptide conjugates of the invention before and after entering cells can be determined by direct operator visualization. The fluorescence microscope provides an excitation light source to induce fluorescence of the donor dye, and transfer of energy to the acceptor dye of a peptide conjugate. The microscope may be equipped with a camera, a photometer, or an image acquisition system. The microscope, or other detection device, may be mated with a robotic plate handler to load and unload a series of plates or arrays of cells.

Alternatively, the methods of the invention may be conducted by flow cytometry where cells move in a fluid past a laser beam. The laser beam excites and detects fluorescent dyes. Data which enumerates the fluorescence intensities from each cell may be gathered by a flow cytometer instrument, or another instrument performing fluorescence activated cell sorting (FACS).

VI.10 DATA ANALYSIS OF FLUORESCENCE DETECTION OF CASPASE ACTIVITY

Two channels of fluorescence intensity data from the images created from spot are digitized. FIG. 9 shows the image data from the FMAT 8100 with gray scale (top) and two-color (bottom) images from representative wells containing peptide conjugate 9 and NT-2 cells. Red and blue are pseudo-colors, arbitrarily assigned to represent the ratio of the fluorescence intensities of channel 2 to channel 1. In the bottom panels of FIG. 9, red cell images correspond to a channel 2/channel 1 fluorescence intensity ratio of >0.5 and blue cell images correspond to a channel 2/channel 1 fluorescence intensity ratio of <0.5. Channel 2 measures emission fluorescence from 685-720 nm and channel 1 measures emission fluorescence from 650-685 nm. The ratio of channel 2/channel 1 fluorescence intensity inversely correlates with the percentage of cells which are apoptotic. Emission from the diamino-benzophenoxazine acceptor dye 3 (Em. max 709 nm, FIG. 5b, $DYE^2$) is primarily detected in the second channel. Emission from the dibenzorhodamine donor dye 1 (Abs. max 637 nm, Em. max 652 nm, FIG. 5b, $DYE^1$) is primarily detected in the first channel.

In FIG. 9, the untreated NT-2 cells (left) are non-apoptotic. No caspase activity is evident because only emission from the acceptor dye is detected due to quenching of the donor dye in the intact, uncleaved peptide conjugate 9. The negative control samples (left) provide a baseline, background fluorescence image and measurement. When the cells are treated with 500 nM camptothecin to induce apoptosis (middle), caspase activity is evident due to the production of emission from the donor dye, indicated by blue images. When the experiment is conducted with 500 nM camptothecin, and a caspase inhibitor (right), again no caspase activity is evident based upon display of red images only. Addition of the caspase inhibitor shows specificity of 9 for caspase-3. Suppression of channel 1 fluorescence is evidence of the specificity of peptide conjugate 9 as a substrate for caspase.

The caspase inhibitor is a peptide, DEVD, modified at the carboxyl terminus as a fluoromethyl ketone (FMK). Z-DEVD-FMK (Enzyme Systems Products, Livermore, Calif.) is known to be a recognition-site specific inhibitor of caspase:

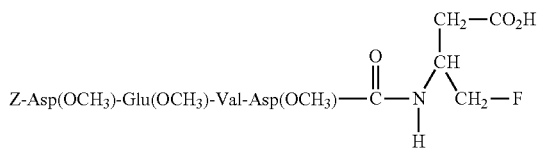

Another caspase inhibitor, is Z-VAD-FMK (Enzyme Systems Products, Livermore, Calif.):

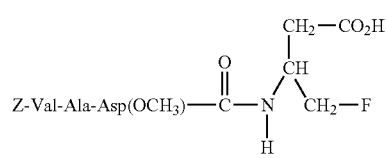

These caspase inhibitors bear the benzyloxycarbonyl group (Z) at the amino terminus and methyl esters ($OCH_3$) on the aspartic acid and glutamic acid side chains to enhance cell permeability (FIG. 10).

Before or after cleavage, the peptide conjugate or peptide fragments bearing the diamino-benzophenoxazine acceptor dye may bind to nucleic acids. The quantum yield of diamino-benzophenoxazine dyes increases thirty-fold upon binding to nucleic acids (Yan, U.S. Pat. No. 6,140,500). It can be seen that before apoptosis (left), channel 2 red images of live cells are more numerous and smaller than after apoptosis (middle) where the nuclei are disrupted and DNA diffuses throughout the apoptotic cells. Images from the apoptotic cells (middle) are fewer and larger, indicating binding of the diamino-benzophenoxazine dyes to nucleic acids. The diamino-benzophenoxazine dye is highly effective in delivering labelled peptide conjugates into cells. Whereas many peptides require hydrophobic labels, pro-drug groups, esters, or other protecting groups to increase cell permeability, the diamino-benzophenoxazine dye promotes rapid entry into the cell when conjugated to peptides.

A data spreadsheet assigns numerical values of fluorescence intensity and peak heights. The greyscale image has intensity content, like an autoradiogram. The color plot does not have any intensity variability. The cells are simply counted by a cell counting algorithm as either blue or red depending on the ratio of channel 2 to channel 1 fluorescence intensity, and independent of intensity values. The fraction of apoptotic cells is determined by identifying the apoptotic population in each well and dividing by the total number of cells detected. The ratio of red (channel 2) to blue (channel 1) inversely correlates to the apoptotic fraction. In other words:

$$\text{Total apoptotic fraction} = \frac{\text{blue images}}{\text{red images} + \text{blue images}}$$

Measurement of channel 2 from negative controls gives normalizing data. The ratio is plotted as the fraction apoptotic ordinate. Ratiometric analysis correlates with cleavage, apoptosis, and caspase activity. Effects of introducing apoptosis inducers and caspase inhibitors to different cells under variable conditions can thus be measured by the mix-and-read protocols on the FMAT 8100 System. A dose response is determined when this fraction (% apoptotic) is plotted as a function of the concentration of camptothecin in the well (FIG. 11), and other apoptosis inducers (FIGS. 12 and 13).

Qualitative information is also available by counting the number of cells present and observing the shape, morphology and clumping of cells, directly analogous to classical microscope-based histological examination of cells. The acceptor dye may faintly stain the nuclei of cells prior to peptide conjugate cleavage and therefore provides a baseline cell number normalization in channel 2 for the assay. When the peptide conjugate is cleaved, the donor dye is no longer quenched and will fluoresce intensely in channel 1.

Cells treated with caspase inhibitors, DEVD-FMK and Z-VAD-FMK at 50 µM showed complete suppression of cleavage of peptide conjugate 9 (FIG. 10). The dose response of NT-2 cells to varying concentrations of camptothecin was plotted in FIG. 11. The fraction of apoptotic cells correlates with camptothecin concentration. Likewise, doxirubicin show a dose response effect as an apoptosis inducer with detection of caspase activity by cleavage of peptide conjugate 9 (FIG. 12). Above about 0.1 µM doxirubicin, most of the cells were detected as apoptotic. Furthermore, staurosporine induced apoptosis in HeLa and Jurkat cells (FIG. 13). The fraction of apoptotic cells correlates with staurosporine concentration above a threshold of about 0.05 µM in Jurkat cells and 0.5 µM in HeLa cells.

VI.11 SOLID SUPPORT CASPASE ASSAY

A biochemical assay for assaying caspase activity can be conducted with peptide conjugates covalently attached to a solid support. A bead assay on the FMAT 8100 System has been described (Swartzman, Anal. Biochem. (1999), 271(2): 143-51). The solid support can be any bead, particle, or surface which can settle, reside, or be attached within the scanning area of the FMAT laser. As in the intracellular assay methods, when the recognition site of a peptide conjugate is cleaved by caspase, peptide fragments result. The peptide conjugate bound to the support is designed such that upon cleavage, the peptide fragment bearing the donor dye remains covalently attached on the solid support, e.g. a bead. The bead settles into the detection area of the vessel and its fluorescence can be detected and measured. One critical parameter of a bead-based assay is the density of the bead. The support must be more dense than the solution, so that sufficient settling will occur within a useful time bead will settle. The peptide fragment bearing the acceptor dye remains in solution and is not detected, or its fluorescence can be discriminated in systems which measure fluorescence in solution, e.g. plate readers. Alternatively, the peptide fragment remaining covalently attached on the solid support bears the acceptor dye, which is detected and measured after cleavage. Baseline fluorescence and normalization can be established with negative controls not containing caspase or before a caspase is introduced.

Nucleic acids can be introduced for binding by the diamino-benzophenoxazine peptide fragment after cleavage to gain the sensitivity advantage from the quantum yield increase upon binding. Cell lysates containing caspase can be introduced in vessels containing peptide conjugates on solid support. Small molecule caspase inhibitors can be rapidly screened by this method with scoring by measuring fluorescence intensity.

VI.12 KITS

The invention includes kits comprising the peptide conjugates and other reagents, such as an apoptosis inducer, a caspase inhibitor, and cells. Kits include peptide conjugates and reagents necessary to conduct the assay methods of the invention. Kits also include a polypeptide and a dibenzorhodamine or diamino-benzophenoxazine dye labelling reagent.

VI.13 EXAMPLES

The invention will be further clarified by a consideration of the following examples, which are intended to be purely exemplary of the invention and not to in any way limit its scope.

Generally, reverse-phase HPLC was conducted under the following conditions: Flow rate: 4 ml/min. Mobile phases: Buffer A: 0.1% TFA in water; Buffer B: 0.085% TFA in acetonitrile. Gradient: Buffer B was linearly increased from 0% (100% Buffer A) to 70% (30% Buffer A) in 15 minutes; Buffer B was then linearly increased to 100% in 2 minutes. After running with Buffer B for 2 minutes, Buffer B was linearly decreased to 0% in 2 minutes. Detector: 630 nm (or 280 nm if compounds were not red-fluorescent dyes).

Example 1

Synthesis of NHS Ester 2

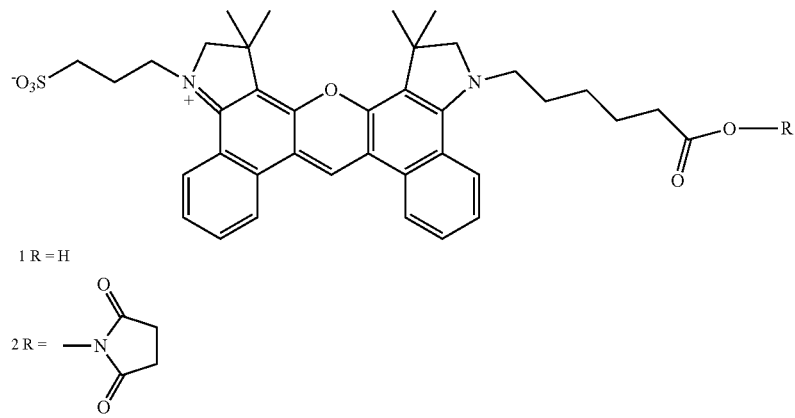

1 R = H

2 R = (N-succinimidyl)

The trifluoroacetate salt of dibenzorhodamine dye 1 (U.S. Pat. Nos. 5,936,087; 6,051,719 and "Sulfonated Diarylrhodamine Dyes", Ser. No. 09/724,855, filed Nov. 28, 2000, each of which is incorporated by reference) was dissolved (10 mg, 16 μmol) in 2 ml dry DMF under argon at room temperature. O—(N-Succinimidyl)-N,N,N',N'-tetramethyluronium tetrafluoroborate (TSTU, Fluka, 60 mg, 200 μmol) and triethylamine (Aldrich, 2.0 μl, 14 μmol) were added. The mixture was stirred at room temperature for 30 minutes. The NHS ester product 2 was purified by reverse-phase HPLC. According to HPLC analysis, all of 1 was converted to NHS 2. In aqueous, neutral buffer (about pH 7), the absorbance maximum wavelength of acid 1, NHS 2, and the dibenzorhodamine dye when labelled to a polypeptide, e.g. 9, was about 637 nm. The emission maximum wavelength was about 652 nm.

Example 2

Synthesis of NHS Ester 4

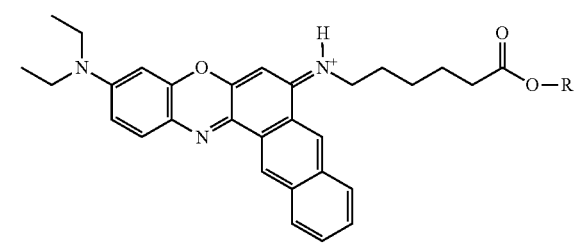

3 R = H

4 R = 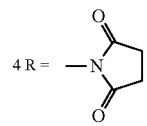

By the same protocol as Example 1, benzophenoxazine dye 3 (Yan, U.S. Pat. No. 6,140,500; "Sulfonated [8,9]Benzophenoxazine Dyes And The Use Of Their Labelled Conjugates" Ser. No. 09/564,417, filing date May 2, 2000) was converted to NHS ester dye 4. In aqueous, neutral buffer (about pH 7), the absorbance maximum wavelength of acid 3, NHS 4, and the diamino-benzophenoxazine dye when labelled to a polypeptide, e.g. 9, was about 655 nm. The emission maximum wavelength was about 709 nm. Mass spectroscopy 4 ($C_{34}H_{35}N_4O_5$): M+1 calculated: 579.3. found: 579.3.

Example 3

Synthesis of Peptide Conjugate 9

Peptide resin, Fmoc-Gly-Asp(t-But)-Glu(t-But)-Val-Asp(t-But)-Gly-Ile-Lys(Dde)-PAL-PS Resin 5, was synthesized by FastMoc™ chemistry on a Model 433 Peptide Synthesizer (Applied Biosystems, Foster City, Calif.) at a 10 μmole scale (FIG. 3). The Dde (4,4-dimethyl-2,6-dioxocyclohex-1-ylidene-ethyl) group was removed from the side-chain amino group of lysine by treatment of the resin with 1% hydrazine in DMF at room temperature for 1 hour. The peptide resin was then reacted with the dye NHS 2 to form mono-labelled peptide 6 on the resin (FIG. 3). The Fmoc group was removed from 6 with piperidine in DMF to form the mono dye-labelled peptide 7, which was cleaved and deprotected with a mixture of trifluoroacetic acid:thioanisole:water (90:5:5) for 1 hour at room temperature to give deprotected mono-labelled peptide 8 (FIG. 4). Peptide 8 was purified with reverse-phase HPLC and dissolved in 0.1 M aqueous NaHCO₃. NHS dye 4 was added in an approximately equal volume of acetonitrile. After reacting for 10 min, peptide conjugate 9 was isolated by purification by reverse-phase HPLC (FIG. 5). Peptide conjugate 9 ($C_{102}H_{127}N_{15}O_{21}S$) was characterized with Electrospray Mass Spectroscopy (PE Sciex): Calculated exact mass: 1929.91. Found: (M+H) 1932.04; (M/2+H) 966.80; (M/3+H) 644.79; (M/4+H) 483.52. Final estimated mass: 1931.00. Standard deviation: 0.68.

9

DYE²-Gly-Asp-Glu-Val-Asp-Gly-Ile-Lys-DYE¹  SEQ ID. NO. 2

See FIG. 5b for the structures of DYE¹ and DYE².

Example 4

Synthesis of Peptide Conjugate 12

Peptide conjugate 12 was synthesized by the methods of Example 3.

12

DYE²-Gly-Leu-Glu-Thr-Asp-Gly-Ile-Lys-DYE¹  SEQ ID. NO. 3

See FIG. 5b for the structures of DYE¹ and DYE². Peptide conjugate 12 is a caspase-8 substrate. Peptide conjugate 12 ($C_{103}H_{131}N_{15}O_{20}S$) was characterized with Electrospray Mass Spectroscopy (PE Sciex): Calculated exact mass: 1929.94. Found: (M+H) 1931.04; (M/2+H) 966.55. Final estimated mass: 1930.55. Standard deviation: 0.74.

Example 5

In Vitro Cleavage of Peptide Conjugate 9 with Caspase-3

5 µl Peptide conjugate 9 (39.2 µM) was incubated in 190 µl of Assay Buffer (50 mM Tris, 100 mM NaCl, 10 mM DTT, 1 mM EDTA, 0.1% (w/v) CHAPS and 10% sucrose, pH 7.2) and 5 µl of 10 ng/µl of purified caspase-3 (BD PharMingen, Franklin Lakes, N.J.) in Enzyme Dilution Buffer (50 mM Tris, 100 mM NaCl and 50 mM imidazole, pH 8.0) for 1.5 hours. The final concentrations of 9 and cleavage products 10 and 11 were each 0.98 µM. The excitation spectrum of the mixture of products 10 and 11 was measured between 550 and 680 nm with emission wavelength set at 700 nm (FIG. 6). The emission spectrum was measured between 620 and 740 nm with excitation wavelength set at 600 nm (FIG. 7). Spectra were measured with a Perkin-Elmer LS50B fluorimeter (Norwalk, Conn.). The excitation and emission spectra were measured under the same conditions and parameters minus the 5 µl of caspase-3 and the addition of 5 µl of Enzyme Dilution buffer.

Data from the time course of cleavage of 9 with caspase-3 was collected with the excitation and emission wavelengths set at 630 nm and 650 nm respectively. The caspase-3 was introduced in the Enzyme Dilution buffer after the fluorescence intensity had stabilized. The fluorescence intensity over the first 10 minutes is plotted in FIG. 8.

Example 6

Intracellular Caspase Assay Conducted on the FMAT™ 8100 HTS System with Peptide Conjugate 9

NT-2 cells stored in the freezer were grown in RPMI 1640/10% FBS media at 37° C., expanding the population by growing to log phase. The cells were plated at 5,000-10,000 cells/well in 100 µl/well, and left to attach to the wells overnight. The cells were treated with varying doses of camptothecin (CMP) in DMSO in an additional 100 µl. Camptothecin was serially diluted from 3 µM in DMSO (final camptothecin concentration in the well), performing 10 serial 3-fold dilutions and added in a volume of 100 µl. The final two columns of wells in the plate were left untreated (media only added). The plate was incubated for 24 hours. Peptide conjugate 9 was resuspended in 100 µl of 1:1 $CH_3CN:H_2O$ and 0.01% TFA to a concentration of 1 mM and vortexed to dissolve completely. Peptide conjugate 9 was diluted in media to a concentration of 12.5 µM (5×). Fifty µl of peptide conjugate in media was added to every well. The plate was incubated at 37° C. for 90 minutes. The plate was scanned on the FMAT 8100 system.

All publications, patents, and patent applications referred to herein are hereby incorporated by reference, and to the same extent as if each individual publication, patent or patent application was specifically and individually indicated to be incorporated by reference.

Although only a few embodiments have been described in detail above, those having ordinary skill in the chemical arts will clearly understand that many modifications are possible in these embodiments without departing from the teachings thereof. All such modifications are intended to be encompassed within the scope of the following claims.

We claim:

1. A method of synthesizing a peptide conjugate comprising:
   a) synthesizing a polypeptide on a solid support, wherein the polypeptide comprises the amino acid sequence, Gly-Asp-Glu-Val-Asp-Gly-Ile-Lys (SEQ ID NO. 2);
   b) reacting the polypeptide on a solid support with a first dye labelling reagent;
   c) cleaving the polypeptide from the solid support; and
   d) reacting the cleaved polypeptide with a second dye labelling reagent;
   wherein the first dye labelling reagent is of the formula:

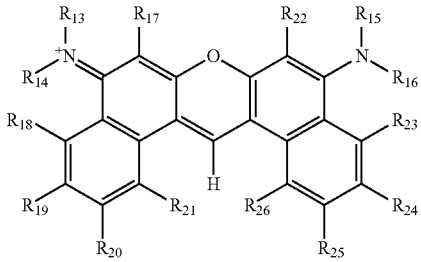

wherein $R_{13}$, $R_{14}$, $R_{15}$, and $R_{16}$ are selected from hydrogen, $C_1$-$C_{12}$ alkyl, $C_1$-$C_{12}$ alkyldiyl, phenyl, substituted phenyl, benzyl, substituted benzyl, biphenyl, substituted biphenyl, naphthyl, substituted naphthyl, heterocycle, substituted heterocycle, a water-solubilizing group and a linking moiety;
$R_{13}$ when taken together with $R_{14}$ is $C_2$-$C_8$ alkyldiyl;
$R_{15}$ when taken together with $R_{16}$ is $C_2$-$C_8$ alkyldiyl;
$R_{13}$ when taken together with $R_{17}$ is $C_2$-$C_8$ alkyldiyl;
$R_{15}$ when taken together with $R_{22}$ is $C_2$-$C_8$ alkyldiyl;
$R_{17}$, $R_{18}$, $R_{19}$, $R_{20}$, $R_{21}$, $R_{22}$, $R_{23}$, $R_{24}$, $R_{25}$, and $R_{26}$ are selected from hydrogen, fluorine, chlorine, bromine, $C_1$-$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), primary amino (—$NH_2$), ammonium (—$NH_3^+$), secondary amino (—NHR), tertiary amino (—$NR_2$), quaternary amine (—$NR_3^+$), amido (—$CONR_2$), nitrile (—CN), nitro (—$NO_2$), $C_1$-$C_8$ alkoxy (—OR), phenoxy, phenolic, tolyl, phenyl, $C_5$-$C_{20}$ aryl, benzyl, heterocycle, phosphonate, phosphate, sulfate, polyethyleneoxy, a water-solubilizing group, and a linking moiety, wherein R is selected from $C_1$-$C_6$ alkyl and $C_1$-$C_6$ alkyldiyl, and Ar is $C_5$-$C_{14}$ aryl;
$R_{19}$ and $R_{20}$, when taken together, are $C_5$-$C_{14}$ aryleno;
$R_{24}$ and $R_{25}$, when taken together, are $C_5$-$C_{14}$ aryleno;
with the proviso that at least one of $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, and $R_{26}$ is a linking moiety; and the second labelling reagent is of the formula:

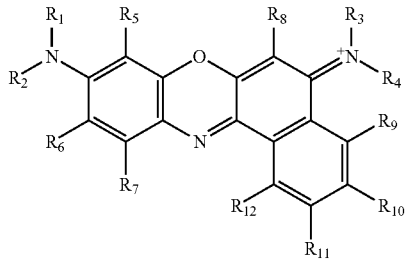

wherein $R_1$, $R_2$, $R_3$, and $R_4$ are selected from hydrogen, $C_1$-$C_{12}$ alkyl, $C_1$-$C_{12}$ alkyldiyl, phenyl, substituted phenyl, benzyl, substituted benzyl, biphenyl, substituted biphenyl, naphthyl, substituted naphthyl, heterocycle, substituted heterocycle, a water-solubilizing group, and a linking moiety;
$R_1$ when taken together with $R_2$ is $C_2$-$C_8$ alkyldiyl;
$R_3$ when taken together with $R_4$ is $C_2$-$C_8$ alkyldiyl;
$R_5$, $R_6$, $R_7$, $R_8$, $R_9$, $R_{10}$, $R_{11}$, and $R_{12}$ are selected from hydrogen, fluorine, chlorine, bromine, $C_1$-$C_8$ alkyl, carboxylate, sulfate, sulfonate, alkylsulfonate, aminomethyl (—$CH_2NH_2$), aminoalkyl, 4-dialkylaminopyridinium, hydroxymethyl (—$CH_2OH$), methoxy (—$OCH_3$), hydroxyalkyl (—ROH), thiomethyl (—$CH_2SH$), thioalkyl (—RSH), alkylsulfone (—$SO_2R$), arylthio (—SAr), arylsulfone (—$SO_2Ar$), sulfonamide (—$SO_2NR_2$), alkylsulfoxide (—SOR), arylsulfoxide (—SOAr), primary amino (—$NH_2$), ammonium (—$NH_3^+$), secondary amino (—NHR), tertiary amino (—$NR_2$), quaternary amine (—$NR_3^+$), amido (—$CONR_2$), nitrile (—CN), nitro (—$NO_2$), $C_1$-$C_8$ alkoxy (—OR), phenoxy, phenolic, tolyl, phenyl, $C_5$-$C_{20}$ aryl, benzyl, heterocycle, phosphonate, phosphate, sulfate, polyethyleneoxy, a water-solubilizing group, and a linking moiety, wherein R is selected from $C_1$-$C_6$ alkyl and $C_1$-$C_6$ alkyldiyl, and Ar is $C_5$-$C_{14}$ aryl;
$R_6$ and $R_7$, when taken together, is $C_5$-$C_{14}$ aryleno;
$R_{10}$ and $R_{11}$, when taken together, is $C_5$-$C_{14}$ aryleno;
with the proviso that at least one of $R_1$, $R_2$, $R_3$, $R_4$, $R_5$, $R_6$, $R_7$, $R_8$, $R_9$, $R_{10}$, $R_{11}$, and $R_{12}$ is a linking moiety;
whereby a peptide conjugate is formed.

2. A kit comprising the peptide conjugate of claim 1 and a plurality of eukaryotic cells.

* * * * *